(12) United States Patent
Tracey et al.

(10) Patent No.: US 9,592,228 B2
(45) Date of Patent: *Mar. 14, 2017

(54) TREATMENT OF INFLAMMATION USING ALPHA 7 RECEPTOR-BINDING AGONISTS

(71) Applicant: THE FEINSTEIN INSTITUTE FOR MEDICAL RESEARCH, Manhasset, NY (US)

(72) Inventors: Kevin J. Tracey, Old Greenwich, CT (US); Hong Wang, Havertown, PA (US)

(73) Assignee: The Feinstein Institute for Medical Research, Manhasset, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/844,652

(22) Filed: Sep. 3, 2015

(65) Prior Publication Data

US 2015/0359785 A1 Dec. 17, 2015

Related U.S. Application Data

(63) Continuation of application No. 13/019,053, filed on Feb. 1, 2011, now abandoned, which is a continuation of application No. 12/724,888, filed on Mar. 16, 2010, now abandoned, which is a continuation of application No. 11/724,605, filed on Mar. 15, 2007, now Pat. No. 7,785,808, which is a continuation of application No. 10/957,426, filed on Sep. 30, 2004, now Pat. No. 7,238,715, which is a continuation-in-part of application No. 10/729,427, filed on Dec. 5, 2003, now Pat. No. 7,273,872.

(60) Provisional application No. 60/431,650, filed on Dec. 9, 2002.

(51) Int. Cl.
| | | |
|---|---|---|
| A01N 43/42 | (2006.01) |
| A61K 31/46 | (2006.01) |
| A61K 31/00 | (2006.01) |
| A61K 31/439 | (2006.01) |
| A61K 31/444 | (2006.01) |
| G01N 33/68 | (2006.01) |
| G01N 33/94 | (2006.01) |

(52) U.S. Cl.
CPC ............ *A61K 31/46* (2013.01); *A61K 31/00* (2013.01); *A61K 31/439* (2013.01); *A61K 31/444* (2013.01); *G01N 33/6863* (2013.01); *G01N 33/9406* (2013.01); *G01N 2333/525* (2013.01); *G01N 2333/54* (2013.01)

(58) Field of Classification Search
USPC ......................................................... 514/278
IPC ................................. A01N 43/42; A61K 31/48
See application file for complete search history.

(56) References Cited

PUBLICATIONS

Pereira et al., J Pharmacol Exp Ther. Jun. 1993;265(3):1474-1491.*
Tamamizu et al., (Biochemistry, 1996, 35 (36), pp. 11773-11781).*

* cited by examiner

*Primary Examiner* — Shirley V Gembeh
(74) *Attorney, Agent, or Firm* — Saul Ewing LLP; Kathryn Doyle; Domingos J. Silva

(57) ABSTRACT

Methods of inhibiting release of a proinflammatory cytokine from a macrophage are provided. The methods comprise treating the macrophage with a cholinergic agonist in an amount sufficient to decrease the amount of the proinflammatory cytokine that is released from the macrophage, wherein the cholinergic agonist is selective for an α7 nicotinic receptor. Methods for inhibiting an inflammatory cytokine cascade in a patient are also provided. The methods comprise treating the patient with a cholinergic agonist in an amount sufficient to inhibit the inflammatory cytokine cascade, wherein the cholinergic agonist is selective for an α7 nicotinic receptor. Methods for determining whether a compound is a cholinergic agonist reactive with an α7 nicotinic receptor are also provided. The methods comprise determining whether the compound inhibits release of a proinflammatory cytokine from a mammalian cell. Additionally, methods for determining whether a compound is a cholinergic antagonist reactive with an α7 nicotinic receptor are provided. These methods comprise determining whether the compound reduces the ability of a cholinergic agonist to inhibit the release of a proinflammatory cytokine from a mammalian cell. Oligonucleotides or mimetics capable of inhibiting attenuation of lipopolysaccharide-induced TNF release from a mammalian macrophage upon exposure of the macrophage to a cholinergic agonist are also provided. The oligonucleotides or mimetics consist essentially of a sequence greater than 5 nucleotides long that is complementary to an mRNA of an α7 receptor. Additionally, methods of inhibiting attenuation of TNF release from a mammalian macrophage upon exposure of the macrophage to a cholinergic agonist are provided. These methods comprise treating the macrophage with the above-described oligonucleotide or mimetic.

20 Claims, 11 Drawing Sheets

Blockade of TNF production in LPS stimulated RAW264.7 cells

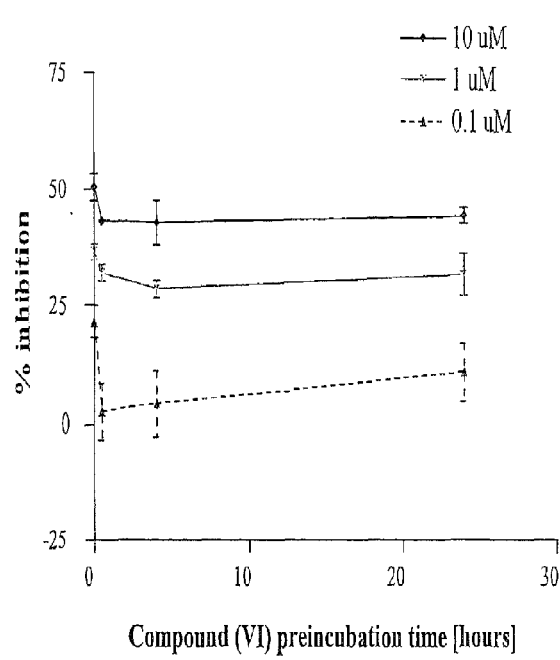
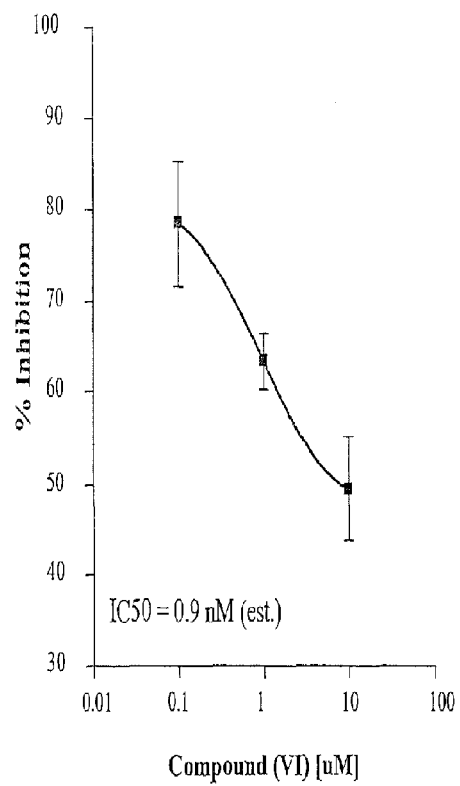
FIG. 8A
FIG. 8B

```
                             SEQUENCE LISTING

<160> NUMBER OF SEQ ID NOS: 21

<210> SEQ ID NO 1
<211> LENGTH: 22
<212> TYPE: DNA
<213> ORGANISM: Artificial Sequence
<220> FEATURE:
<223> OTHER INFORMATION: sense primer for alpha1 subunit of nicotinic
      acetylcholine receptor

<400> SEQUENCE: 1
ccagacctga gcaacttcat gg                                                  22

<210> SEQ ID NO 2
<211> LENGTH: 22
<212> TYPE: DNA
<213> ORGANISM: Artificial Sequence
<220> FEATURE:
<223> OTHER INFORMATION: antisense primer for alpha1 subunit of
      nicotinic acetylcholine receptor

<400> SEQUENCE: 2
aatgagtcga cctgcaaaca cg                                                  22

<210> SEQ ID NO 3
<211> LENGTH: 21
<212> TYPE: DNA
<213> ORGANISM: Artificial Sequence
<220> FEATURE:
<223> OTHER INFORMATION: sense primer for alpha subunit of nicotinic
      acetylcholine receptor

<400> SEQUENCE: 3
gactgttcgt ttcccagatg g                                                   21

<210> SEQ ID NO 4
<211> LENGTH: 22
<212> TYPE: DNA
<213> ORGANISM: Artificial Sequence
<220> FEATURE:
<223> OTHER INFORMATION: antisense primer for alpha subunit of nicotinic
      acetylcholine receptor

<400> SEQUENCE: 4
acgaagttgg gagccgacat ca                                                  22

<210> SEQ ID NO 5
<211> LENGTH: 22
<212> TYPE: DNA
<213> ORGANISM: Artificial Sequence
<220> FEATURE:
<223> OTHER INFORMATION: sense primer for alpha9 subunit of nicotinic
      acetylcholine receptor
```

<400> SEQUENCE: 5
cgagatcagt acgatggcct ag                                          22

<210> SEQ ID NO 6
<211> LENGTH: 22
<212> TYPE: DNA
<213> ORGANISM: Artificial Sequence
<220> FEATURE:
<223> OTHER INFORMATION: antisense primer for alpha9 subunit of
      nicotinic acetycholine receptor

<400> SEQUENCE: 6
tctgtgacta atccgctctt gc                                          22

<210> SEQ ID NO 7
<211> LENGTH: 22
<212> TYPE: DNA
<213> ORGANISM: Artificial Sequence
<220> FEATURE:
<223> OTHER INFORMATION: sense primer for alpha1subunit of nicotinic
      acetycholine receptor

<400> SEQUENCE: 7
atcacctacc acttcgtcat gc                                          22

<210> SEQ ID NO 8
<211> LENGTH: 22
<212> TYPE: DNA
<213> ORGANISM: Artificial Sequence
<220> FEATURE:
<223> OTHER INFORMATION: antisense primer for alpha1 subunit of
      nicotinic acetylcholine receptor

<400> SEQUENCE: 8
gtatgtggtc catcaccatt gc                                          22

<210> SEQ ID NO 9
<211> LENGTH: 22
<212> TYPE: DNA
<213> ORGANISM: Artificial Sequence
<220> FEATURE:
<223> OTHER INFORMATION: sense primer for alpha7 ubunit of nicotinic
      acetylcholine receptor

<400> SEQUENCE: 9
cccggcaaga ggagtgaaag gt                                          22

<210> SEQ ID NO 10
<211> LENGTH: 20
<212> TYPE: DNA
<213> ORGANISM: Artificial Sequence
<220> FEATURE:
<223> OTHER INFORMATION: antisense primer for alpha7 subunit of
      nicotinic acetylcholine receptor

<400> SEQUENCE: 10
tgcagatgat ggtgaagacc                                             20

<210> SEQ ID NO 11
<211> LENGTH: 23
<212> TYPE: DNA
<213> ORGANISM: Artificial Sequence
<220> FEATURE:
<223> OTHER INFORMATION: sense primer for alpha subunit of nicotinic
      acetylcholine receptor

<400> SEQUENCE: 11
agagcctgtg aacaccaatg tgg                                              23

<210> SEQ ID NO 12
<211> LENGTH: 22
<212> TYPE: DNA
<213> ORGANISM: Artificial Sequence
<220> FEATURE:
<223> OTHER INFORMATION: antisense primer for alpha subunit of nicotinic
      acetylcholine receptor

<400> SEQUENCE: 12
atgactttcg ccaccttctt cc                                               22

<210> SEQ ID NO 13
<211> LENGTH: 19
<212> TYPE: DNA
<213> ORGANISM: Artificial Sequence
<220> FEATURE:
<223> OTHER INFORMATION: cloning primers for full-length alpha7
      nicotinic acetylcholine receptors

<400> SEQUENCE: 13
aggtgcctct gtggccgca                                                   19

<210> SEQ ID NO 14
<211> LENGTH: 18
<212> TYPE: DNA
<213> ORGANISM: Artificial Sequence
<220> FEATURE:
<223> OTHER INFORMATION: cloning primers for full-length alpha7
      nicotinic acetylcholine receptors

<400> SEQUENCE: 14
gactactcag tggccctg                                                    18

<210> SEQ ID NO 15
<211> LENGTH: 18
<212> TYPE: DNA
<213> ORGANISM: Artificial Sequence
<220> FEATURE:
<223> OTHER INFORMATION: cloning primers for full-length alpha7
      nicotinic acetylcholine receptors

<400> SEQUENCE: 15
cgacacggag acgtggag                                                    18

<210> SEQ ID NO 16
<211> LENGTH: 21
<212> TYPE: DNA
<213> ORGANISM: Artificial Sequence
<220> FEATURE:
<223> OTHER INFORMATION: cloning primers for full-length alpha7
      nicotinic acetylcholine receptors

<400> SEQUENCE: 16
ggtacggatg tgccaaggag t                                                21

<210> SEQ ID NO 17
<211> LENGTH: 30
<212> TYPE: DNA
<213> ORGANISM: Artificial Sequence
<220> FEATURE:
<223> OTHER INFORMATION: cloning primers for full-length alpha7
      nicotinic acetylcholine receptors

<400> SEQUENCE: 17

```
caaggatccg gactcaacat gcgctgctcg                              30

<210> SEQ ID NO 18
<211> LENGTH: 33
<212> TYPE: DNA
<213> ORGANISM: Artificial Sequence
<220> FEATURE:
<223> OTHER INFORMATION: cloning primers for full-length alpha7
      nicotinic acetylcholine receptors

<400> SEQUENCE: 18
cggctcgagt caccagtgtg gttacgcaaa gtc                           33

<210> SEQ ID NO 19
<211> LENGTH: 20
<212> TYPE: DNA
<213> ORGANISM: Artificial Sequence
<220> FEATURE:
<223> OTHER INFORMATION: antisense primer for translation initiation
      regions of alpha7, alpha1 and alpha10

<400> SEQUENCE: 19
gcagcgcatg ttgagtcccg                                         20

<210> SEQ ID NO 20
<211> LENGTH: 20
<212> TYPE: DNA
<213> ORGANISM: Artificial Sequence
<220> FEATURE:
<223> OTHER INFORMATION: antisense primer for translation initiation
      regions of alpha7, alpha1 and alpha10

<400> SEQUENCE: 20
gggctccatg ggctaccgga                                         20

<210> SEQ ID NO 21
<211> LENGTH: 20
<212> TYPE: DNA
<213> ORGANISM: Artificial Sequence
<220> FEATURE:
<223> OTHER INFORMATION: antisense primer for translation initiation
      regions of alpha7, alpha1 and alpha10

<400> SEQUENCE: 21
ccccatggcc ctggcactgc                                         20
```

TREATMENT OF INFLAMMATION USING ALPHA 7 RECEPTOR-BINDING AGONISTS

CROSS-REFERENCE TO RELATED APPLICATIONS

The present application is a continuation of and claims priority to U.S. patent application Ser. No. 13/019,053, filed Feb. 1, 2011, which is a continuation of and claims priority to U.S. patent application Ser. No. 12/724,888, filed Mar. 16, 2010, now abandoned, which is a continuation of and claims priority to U.S. patent application Ser. No. 11/724,605, filed Mar. 15, 2007, now issued as U.S. Pat. No. 7,785,808, which is continuation of and claims priority to U.S. patent application Ser. No. 10/957,426, filed Sep. 30, 2004, now issued as U.S. Pat. No. 7,238,715, which is a continuation-in-part of and claims priority to U.S. patent application Ser. No. 10/729,427, filed Dec. 5, 2003, now issued as U.S. Pat. No. 7,273,872, which claims priority under 35 U.S.C. §119(e) to U.S. Provisional Patent Application No. 60/431,650, filed Dec. 6, 2002, all of which applications are incorporated herein in their entireties.

GOVERNMENT SUPPORT

The invention was supported, in whole or in part, by a grant GM57226 from National Institutes of Health. The Government has certain rights in the invention.

BACKGROUND OF THE INVENTION

The present invention generally relates to methods of reducing inflammation. More specifically, the invention relates to methods of reducing inflammation using α7 receptor-binding cholinergic agonists.

Vertebrates achieve internal homeostasis during infection or injury by balancing the activities of proinflammatory and anti-inflammatory pathways. However, in many disease conditions, this internal homeostasis becomes out of balance. For example, endotoxin (lipopolysaccharide, LPS) produced by all Gram-negative bacteria activates macrophages to release cytokines that are potentially lethal (Tracey et al., 1986; Wang et al., 1999; Nathan, 1987; Dinarello, 1994).

Inflammation and other deleterious conditions (such as septic shock caused by endotoxin exposure) are often induced by proinflammatory cytokines, such as tumor necrosis factor (TNF; also known as TNFα or cachectin), interleukin (IL)-1α, IL-1β, IL-6, IL-8, IL-18, interferon platelet-activating factor (PAF), macrophage migration inhibitory factor (MIF), and other compounds (Thompson, 1998). Certain other compounds, for example high mobility group protein 1 (HMG-1), are induced during various conditions such as sepsis and can also serve as proinflammatory cytokines (PCT publication WO 00/47104). These proinflammatory cytokines are produced by several different cell types, most importantly immune cells (for example monocytes, macrophages and neutrophils), but also non-immune cells such as fibroblasts, osteoblasts, smooth muscle cells, epithelial cells, and neurons (Zhang and Tracey, 1998). Proinflammatory cytokines contribute to various disorders, notably sepsis, through their release during an inflammatory cytokine cascade.

Inflammatory cytokine cascades contribute to deleterious characteristics, including inflammation and apoptosis (Pulkki, 1997), of numerous disorders. Included are disorders characterized by both localized and systemic reactions, including, without limitation, diseases involving the gastrointestinal tract and associated tissues (such as appendicitis, peptic, gastric and duodenal ulcers, peritonitis, pancreatitis, ulcerative colitis, pseudomembranous, acute and ischemic colitis, diverticulitis, epiglottitis, achalasia, cholangitis, coeliac disease, cholecystitis, hepatitis, Crohn's disease, enteritis, and Whipple's disease); systemic or local inflammatory diseases and conditions (such as asthma, allergy, anaphylactic shock, immune complex disease, organ ischemic, reperfusion injury, organ necrosis, hay fever, sepsis, septicemia, endotoxic shock, cachexia, hyperpyrexia, eosinophilic granuloma, granulomatosis, and sarcoidosis); diseases involving the urogential system and associated tissues (such as septic abortion, epididymitis, vaginitis, prostatitis and urethritis); diseases involving the respiratory system and associated tissues (such as bronchitis, emphysema, rhinitis, cystic fibrosis, adult respiratory distress syndrome, pneumonitis, pneumoultramicroscopicsilicovolcanoconiosis, alvealitis, bronchiolitis, pharyngitis, pleurisy, and sinusitis); diseases arising from infection by various viruses (such as influenza, respiratory syncytial virus, HIV, hepatitis B virus, hepatitis C virus and herpes), bacteria (such as disseminated bacteremia, Dengue fever), fungi (such as candidiasis) and protozoal and multicellular parasites (such as malaria, filariasis, amebiasis, and hydatid cysts); dermatological diseases and conditions of the skin (such as burns, dermatitis, dermatomyositis, sunburn, urticaria warts, and wheals); diseases involving the cardiovascular system and associated tissues (such as vasulitis, angiitis, endocarditis, arteritis, atherosclerosis, thrombophlebitis, pericarditis, myocarditis, myocardial ischemia, congestive heart failure, periarteritis nodosa, and rheumatic fever); diseases involving the central or peripheral nervous system and associated tissues (such as Alzheimer's disease, meningitis, encephalitis, multiple sclerosis, cerebral infarction, cerebral embolism, Guillame-Barre syndrome, neuritis, neuralgia, spinal cord injury, paralysis, and uveitis); diseases of the bones, joints, muscles and connective tissues (such as the various arthritides and arthralgias, osteomyelitis, fasciitis, Paget's disease, gout, periodontal disease, rheumatoid arthritis, and synovitis); other autoimmune and inflammatory disorders (such as myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, Type I diabetes, ankylosing spondylitis, Berger's disease, and Retier's syndrome); as well as various cancers, tumors and proliferative disorders (such as Hodgkins disease); and, in any case the inflammatory or immune host response to any primary disease (Gattorno et al., 2000; Yeh and Schuster, 1999; McGuinness et al., 2000; Hsu et al., 1999; Prystowsky and Rege, 1997; Kimmings et al., 2000; Hirano, 1999; Lee et al., 1995; Waserman et al., 2000; Katagiri et al., 1997; Bumgardner and Orosz, 1999; Dibbs et al., 1999; Blum and Miller, 1998; Blackwell and Christman, 1996; Fox, 2000; Carteron, 2000; Hommes and van Deventer, 2000; Gracie et al., 1999; Kanai et al., 2001; Jander and Stoll, 2001; Watanabe et al., 1997; Rayner et al., 2000; Amrani et al., 2000).

Mammals respond to inflammation caused by inflammatory cytokine cascades in part through central nervous system regulation. This response has been characterized in detail with respect to systemic humoral response mechanisms during inflammatory responses to endotoxin (Besedovsky et al., 1986; Woiciechowsky et al., 1998; Hu et al., 1991; Lipton and Catania, 1997). In one set of responses, afferent vagus nerve fibers are activated by endotoxin or cytokines, stimulating the release of humoral anti-inflammatory responses through glucocorticoid hormone release (Watkins and Maier, 1999; Sternberg, 1997; Scheinman et al., 1995). Previous work elucidated a role for vagus nerve signaling as a critical component in the afferent loop that modulates the adrenocorticotropin and fever responses to systemic endotoxemia and cytokinemia (Gaykema et al., 1995; Fleshner et al., 1998; Watkins et al., 1995; Romanovsky et al., 1997).

Another set of responses is through efferent vagus nerve signaling, termed the "cholinergic anti-inflammatory pathway" (Borovikova et al., 2000). Stimulation of the efferent vagus nerve attenuates systemic inflammatory responses and inhibits TNF release (Id.; Bernik et al., 2002; Tracey et al., 2001; U.S. patent application Ser. No. 09/855,446). Acetylcholine, the principle neurotransmitter of the vagus nerve, attenuates macrophage cytokine synthesis by signaling through α-bungarotoxin-sensitive nicotinic acetylcholine receptors, but the identity of the essential macrophage receptor is unknown.

Nicotinic acetylcholine receptors are a family of ligand-gated, pentameric ion channels. In humans, 16 different subunits (α1-7, α9-10, β1-4, δ, ε, and γ) have been identified that form a large number of homo- and hetero-pentameric receptors with distinct structural and pharmacological properties (Lindstrom, 1995; Leonard and Bertrand, 2001; Le Novere and Changeux, 1995). The main known function of this receptor family is to transmit signals for the neurotransmitter acetylcholine at neuromuscular junctions and in the central and peripheral nervous systems (Lindstrom, 1995; Leonard and Bertrand, 2001; Le Novere and Changeux, 1995, Marubio and Changeux, 2000; Steinlein, 1998). Our previous work indicated the presence of α-bungarotoxin-sensitive nicotinic receptors on primary human macrophages (Borovikova et al., 2000), but the identity of the specific receptor subunit was unknown.

Knowledge of the particular nicotinic receptor that is responsible for inhibiting inflammation would be useful to identify specific agonists of the receptor that would inhibit inflammation. Such agonists would be likely to have fewer side effects than currently identified agonists that are relatively non-specific. The identity of other physiological effects influenced by the anti-inflammatory receptor would also be facilitated.

DESCRIPTION OF THE RELATED ART

References Cited

Amrany, Y. et al. Respir. Res. 1:49-53 (2000).
Bernik, T. R. et al. Pharmacological stimulation of the cholinergic anti-inflammatory pathway. J. Exp. Med. 195: 781-788 (2002).
Besedovsky, H. et al. Science 233:652-54 (1986).
Bianchi, M. et al. An inhibitor of macrophage arginine transport and nitric oxide production (CNI-1493) prevents acute inflammation and endotoxin lethality. Mol. Med. 1:254-266 (1995).
Blackwell, T. S. and Christman, S. W. Br. J. Anaesth. 77: 110-17 (1996).
Blum, A. and Miller, H. Am. Heart J. 135:181-86 (1998).
Borovikova, Ivanova, S., Zhang, M., Yang, H., Botchkina, G. I., Watkins, L. R., Wang, H., Abumrad, N., Eaton, J. W. & Tracey, K. J. Vagus nerve stimulation attenuates the systemic inflammatory response to endotoxin. Nature 405:458-462 (2000).
Bumgardner, G. L. and Orosz, C. G. Semin. Liver Dis. 19: 189-204 (1999).
Carteron, N. L. Mol. Med. Today 6:315-23 (2000).
Cohen, P. S. et al. The critical role of p38 MAP kinase in T cell HIV-1 replication. Molecular Medicine 3:339-346 (1997).
Dibbs, Z. et al. Proc. Assoc. Am. Physicians 111:423-28 (1999).
Dinarello, C. A. FASEB J. 8:1314-25 (1994).
Drisdel, R. C. and Green, W. N. Neuronal α-bungarotoxin receptors are α7 subunit homomers. J. Neurosci. 20:133-139 (2000).
Feng, G., Steinbach, J. H. and Sanes, J. R. Rapsyn clusters neuronal acetylcholine receptors but is inessential for formation of an interneuronal cholinergic synapse. J. Neurosci. 18:4166-4176 (1998).
Fleshner, M. et al. J. Neuroimmunol. 86:134-41 (1998).
Fox, D. A. Arch. Intern. Med. 28:437-444 (2000).
Franceschini, D. et al. Altered baroreflex responses in α7 deficient mice. Behavioural Brain Res. 113:3-10 (2000).
Francis, M. M. et al. Mol. Pharmacol. 60:71-79 (2001).
Gattorno, M. et al. J. Rheumatol. 27:2251-2255 (2000).
Gault, J. et al. Genomic organization and partial duplication of the human α7 neuronal nicotinic acetylcholine receptor gene (CHRNA7). Genomics 52:173-185 (1998).
Gaykema, R. P. et al. Endocrinology 136:4717-4720 (1995).
Gracie, J. A. et al. J. Clin. Invest. 104:1393-1401 (1999).
Holladay et al. Neuronal Nicotinic Acetylcholine Receptors as Targets for Drug Discovery. Journal of Medicinal Chemistry 40:4169-4194 (1997).
Hommes D. W. and van Deventer, S. J. Curr. Opin. Clin. Nutr. Metab. Care 3:191-95 (2000).
Hsu, H. Y. et al. S. Pediatr. Gastroenterol. 29:540-45 (1999).
Hu, X. X. et al. J. Neuroinununol. 31:35-42 (1991).
Jander, S. and Stoll, G. J. Neuroinmiunol. 114:253-58 (2001).
Kanai, T. et al. Digestion 63 Suppl. 1:37-42 (2001).
Katagiri, M. et al. J. Clin, Gastroenterol. 25 Suppl. 1: S211-14 (1997).
Keffer, J. et al. Transgenic mice expressing human tumour necrosis factor: a Predictive genetic model of arthritis. EMBO J. 10:4025-4031 (1991).
Kem, W. R. et al. J. Pharmacol. Exp. Ther. 283:979-992 (1997).
Kimmings, A. N. et al. Eur. J. Surg. 166:700-05 (2000).
Kontoyiannis, D. et al. Impaired on/off regulation of TNF biosynthesis in mice lacking TNF AU-rich elements: implications for joint- and gut-associated immunopathologies: Immunity 10:387-398 (1999).
Kumins, N. H., Hunt, J., Gamelli, R. L. and Filkins, J. P. Partial hepatectomy reduces the endotoxin-induced peak circulating level of tumor necrosis factor in rats. Shock 5:385-388 (1996).
Le Novere, N. & Changeux, J-P. Molecular evolution of the nicotinic acetylcholine receptor: an example of multigene family in excitable cells. J. Mol. Evol. 40:155-172 (1995).
Lee, H. G., et al. Clin. Exp. Immunol. 100:139-44 (1995).
Leonard, S. and Bertrand, D. Neuronal nicotinic receptors: from structure to function. Nicotine & Tobacco Res. 3:203-223 (2001).
Lin, W. et al. Distinct roles of nerve and muscle in postsynaptic differentiation of the neuromuscular synapse. Nature 410:1057-1064 (2001).
Lindstrom, J. M. Nicotinic acetylcholine receptors. In "Hand Book Of Receptors And Channels: Ligand- And Voltage-Gated Ion Channels." Edited by R. Alan North. CRC Press, Inc. (1995).

Marubio, L. M. and Changeux, J-P. Nicotinic acetylcholine receptor knockout mice as animal models for studying receptor function. Eur. J. Pharmacol. 393:113-121 (2000).

McGuinness, P. H. et al. Gut 46:260-69 (2000).

Nathan, C. F. J. Clin. Invest. 79:319-26 (1987).

Orr-Urtreger, A. et al. Mice deficient in the ?7 neuronal nicotinic acetylcholine receptor lack α-bungarotoxin binding sites and hippocampal fast nicotinic currents. J. Neurosci. 17:9165-9171 (1997).

Peng, X. et al. Human α7 acetylcholine receptor: cloning of the α7 subunit from the SH-SY5Y cell line and determination of pharmacological properties of native receptors and functional α7 homomers expressed in *Xenopus oocytes*. Mol. Pharmacol. 45:546-554 (1994).

Pulkki, K. J. Ann Med. 29:339-43 (1997).

Prystowsky, J. B. and Rege, R. V. J. Surg. Res. 71:123-26 (1997).

Rayner, S. A. et al. Clin. Exp. Immunol. 122:109-16 (2000).

Romanovsky, A. A. et al. Am. J. Physiol. 273:R407-13 (1997).

Seguela, P. et al. Molecular cloning, functional properties, and distribution of rat brain α7: a nicotinic cation channel highly permeable to calcium. J. Neurosci. 13:596-604 (1993).

Scheinman, R. I. et al. Science 270:283-86 (1995).

Shoop, R. D., Yamada, N. and Berg, D. K. Cytoskeletal links of neuronal acetylcholine receptors containing α7 subunits. J. Neurosci. 20:4021-4029 (2000).

Shoop, R. D. et al. Synaptically driven calcium transients via nicotinic receptors on somatic spines. J. Neurosci. 21:771-781 (2001).

Simosky, J. K. et al. Biol. Psychiatry 50:493-500 (2001).

Steinlein, O. New functions for nicotine acetylcholine receptors? Behavioural Brain Res. 95:31-35 (1998).

Sternberg, E. M. J. Clin. Invest. 100:2641-47 (1997).

Tsutsui, H. et al. Immunol. Rev. 174:192-209 (2000).

Tracey, K. J. et al. Shock and tissue injury induced by recombinant human cachectin. Science 234:470-474 (1986).

Tracey, K. J., Czura, C. J. and Ivanova, S. Mind over immunity. FASEB J. 15:1575-1576 (2001).

Vijayaraghavan, S. et al. Nicotinic receptors that bind α-bungarotoxin on neurons raise intracellular free Ca2+. Neuron 8:353-362 (1992).

Wang, H. et al. HMG-1 as a late mediator of endotoxin lethality in mice. Science 285:248-251 (1999).

Waserman, S. et al. Can. Respir. J. 7:229-37 (2000).

Watanabe, H. et al. J. Reconstr. Microsurg. 13:193-97 (1997).

Watkins, L. R, and Maier, S. F. Proc. Natl. Acad. Sci. USA 96:7710-13 (1999).

Watkins L. R., et al. Neurosci. Lett. 183:27-31 (1995).

Woiciechowsky, C. et al. Nat. Med. 4: 808-13 (1998).

Yeh, S. S. and Schuster, M. W. Am. J. Clin. Nutr. 70, 183-97 (1999).

Zhang and Tracey, in The Cytokine Handbook, 3$^{rd}$ ed., Ed. Thompson, Academic Press, 515-47 (1998).

PCT Patent Application Publication WO 97/30998.

PCT Patent Application Publication WO 00/47104.

PCT Patent Application Publication WO 01/85727.

PCT Patent Application Publication WO 02/44176.

PCT Patent Application Publication WO 02/057275.

U.S. patent application Ser. No. 09/855,446.

U.S. Patent Application Publication No. 2002/0040035.

U.S. Patent Application Publication No. 2002/0086871.

U.S. Pat. No. 5,902,814.

U.S. Pat. No. 5,977,144.

U.S. Pat. No. 6,110,914.

U.S. Pat. No. 6,407,095.

U.S. Pat. No. 6,436,909.

SUMMARY OF THE INVENTION

Accordingly, the present invention is based on the discovery that the α7 receptor is the α-bungarotoxin sensitive receptor that influences the release of proinflammatory cytokines from macrophages. With that knowledge, various methods and compositions would be understood to be useful for treatment of inflammatory conditions and identification of useful compounds for that treatment. Studies of macrophage responses to cholinergic agonists and antagonists are also facilitated by this knowledge.

Thus, the present invention is directed to methods of inhibiting release of a proinflammatory cytokine from a macrophage. The methods comprise treating the macrophage with a cholinergic agonist in an amount sufficient to decrease the amount of the proinflammatory cytokine that is released from the macrophage, wherein the cholinergic agonist is selective for an α7 nicotinic receptor.

In other embodiments, the invention is directed to methods of inhibiting an inflammatory cytokine cascade in a patient. The methods comprise treating the patient with a cholinergic agonist in an amount sufficient to inhibit the inflammatory cytokine cascade, wherein the cholinergic agonist is selective for an α7 nicotinic receptor. In these embodiments, the patient is preferably suffering from, or at risk for, a condition mediated by the inflammatory cytokine cascade.

Additionally, the invention is directed to methods for determining whether a compound is a cholinergic agonist selective for an α7 nicotinic receptor. The methods comprise determining whether the compound inhibits release of a proinflammatory cytokine from a mammalian cell, and determining whether the compound is a cholinergic agonist reactive with at least one nicotinic receptor that is not α7. In these methods, a compound that inhibits the release of the proinflammatory cytokine from the mammalian cell, but is not a cholinergic agonist reactive with at least one nicotinic receptor that is not α7, is a cholinergic agonist selective for an α7 nicotinic receptor.

In related embodiments, the invention is directed to methods for determining whether a compound is a cholinergic antagonist reactive with an α7 nicotinic receptor. These methods comprise determining whether the compound reduces the ability of a cholinergic agonist to inhibit the release of a proinflammatory cytokine from a mammalian cell. In these methods, a compound that reduces the ability of a cholinergic agonist to inhibit the release of a proinflammatory cytokine from a mammalian cell is a cholinergic antagonist reactive with an α7 receptor.

In additional embodiments, the invention is directed to methods for determining whether a test compound has the ability to inhibit inflammation. These methods comprise determining whether the test compound is a cholinergic agonist reactive with an α7 nicotinic receptor.

Other methods for determining whether a test compound has the ability to inhibit inflammation are also part of the invention. These methods comprise determining whether the test compound inhibits binding of an antagonist to an α7 nicotinic receptor.

The present invention is also directed to oligonucleotides or mimetics capable of inhibiting attenuation of lipopolysaccharide-induced TNF release from a mammalian macrophage upon exposure of the macrophage to a cholinergic agonist. The oligonucleotides or mimetics consist essentially of a sequence greater than 5 nucleotides long that is complementary to an mRNA of an α7 receptor.

Additionally, the invention is directed to methods of inhibiting attenuation of TNF release from a mammalian macrophage upon exposure of the macrophage to a cholinergic agonist. These methods comprise treating the macrophage with the above-described oligonucleotide or mimetic.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 8A is a plot showing percent inhibition of LPS-induced release of TNF-α from murine RAW 264.7 macrophage-like cells treated with incremental concentrations of compound (VI) as a function of pre-incubation time.

FIG. 8B is a plot showing percent inhibition of LPS-induced release of TNF-α from murine RAW 264.7 macrophage-like cells treated with incremental concentrations of compound (VI) as a function of concentration of compound (VI).

DETAILED DESCRIPTION OF THE INVENTION

Figure 1:
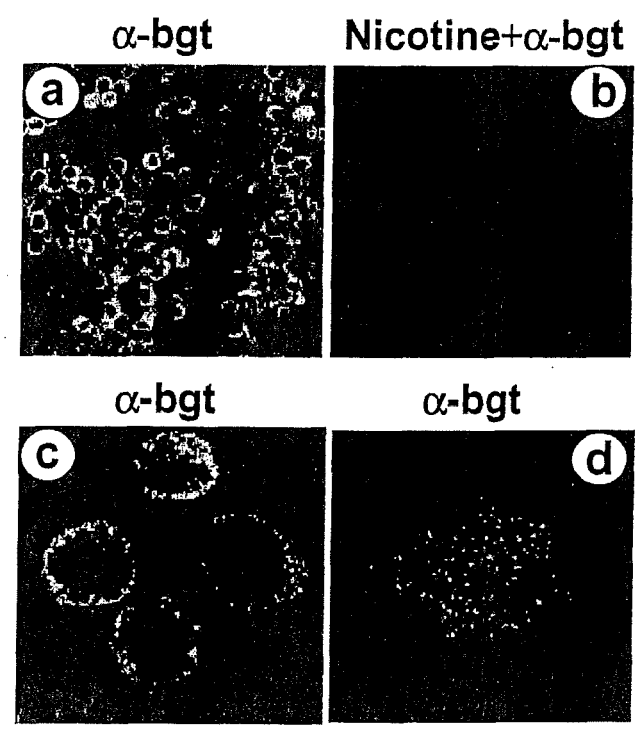
FIG. 1 is fluorescent micrographs establishing that α-bungarotoxin-binding nicotinic receptors are clustered on the surface of macrophages. Primary human macrophages were stained with FITC-labeled α-bungarotoxin (α-bgt, 1.5 μg/ml) and viewed with a fluorescent confocal microscope. Panels 1a and b show lower magnification micrographs. a. cells were stained with α-bungarotoxin alone. b. 500 μM of nicotine was added prior to the addition of α-bungarotoxin. Panels 1c and 1d show higher magnification micrographs to reveal the receptor clusters. c. Focus planes were on the inside layers close to the middle (three lower cells) or close to the surface (upper cell) of cells. d. Focus plane was on the upper surface of the cell.

A description of preferred embodiments of the invention follows.

DEFINITIONS OF SUBSTITUENTS

The term "alkyl", as used herein, unless otherwise indicated, includes saturated monovalent hydrocarbon radicals having straight or branched moieties, typically $C_1$-$C_{10}$, preferably $C_1$-$C_6$. Examples of alkyl groups include, but are not limited to, methyl, ethyl, propyl, isopropyl, and t-butyl.

The term "alkenyl", as used herein, unless otherwise indicated, includes alkyl moieties having at least one carbon-carbon double bond wherein alkyl is as defined above. Examples of alkenyl include, but are not limited to, ethenyl and propenyl.

The term "alkynyl", as used herein, unless otherwise indicated, includes alkyl moieties having at least one carbon-carbon triple bond wherein alkyl is as defined above. Examples of alkynyl groups include, but are not limited to, ethynyl and 2-propynyl.

The terms "alkoxy", as used herein, means an "alkyl-O—" group, wherein alkyl is as defined above.

The term "cycloalkyl", as used herein, unless otherwise indicated, includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl. "Bicycloalkyl" groups are non-aromatic saturated carbocyclic groups consisting of two rings. Examples of bicycloalkyl groups include, but are not limited to, bicyclo-[2.2.2]-octyl and norbornyl. The term "cycloalkenyl" and "bicycloalkenyl" refer to non-aromatic carbocyclic cycloalkyl and bicycloalkyl moieties as defined above, except comprising of one or more carbon-carbon double bonds connecting carbon ring members (an "endocyclic" double bond) and/or one or more carbon-carbon double bonds connecting a carbon ring member and an adjacent non-ring carbon (an "exocyclic" double bond). Examples of cycloalkenyl groups include, but are not limited to, cyclopentenyl and cyclohexenyl. A non-limiting example of a bicycloalkenyl group is norborenyl. Cycloalkyl, cycloalkenyl, bicycloalkyl, and bicycloalkenyl groups also include groups similar to those described above for each of these respective categories, but which are substituted with one or more oxo moieties. Examples of such groups with oxo moieties include, but are not limited to oxocyclopentyl, oxocyclobutyl, oxocyclopentenyl, and norcamphoryl.

The term "cycloalkoxy", as used herein, unless otherwise indicated, includes "cycloalkyl-O—" group, wherein cycloalkyl is defined above.

The term "aryl", as used herein, refers to carbocyclic group. Examples of aryl groups include, but are not limited to phenyl and naphthyl.

The term "heteroaryl", as used herein, refers to aromatic groups containing one or more heteroatoms (O, S, or N). A heteroaryl group can be monocyclic or polycyclic. The heteroaryl groups of this invention can also include ring systems substituted with one or more oxo moieties. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzothiazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

The foregoing heteroaryl groups may be C-attached or N-attached (where such is possible). For instance, a group derived from pyrrole may be pyrrol-1-yl (N-attached) or pyrrol-3-yl (C-attached).

In the context of the present invention, a bicyclic carbocyclic group is a bicyclic compound holding carbon only as a ring atom. The ring structure may in particular be aromatic, saturated, or partially saturated. Examples of such compounds include, but are not limited to, indanyl, naphthalenyl, azulenyl.

In the context of the present invention, an amino group may be a primary (—$NH_2$), secondary (—$NHR_a$), or tertiary (—$NR_aR_b$), wherein $R_a$ and $R_b$ may be any of the alkyl, alkenyl, alkynyl, alkoxy, cycloalkyl, cycloalkoxy, aryl, heteroaryl, and a bicyclic carbocyclic group.

The practice of the present invention will employ, unless otherwise indicated, conventional techniques of cell culture, molecular biology, microbiology, cell biology, and immunology, which are well within the skill of the art. Such techniques are fully explained in the literature. See, e.g., Sambrook et al., 1989, "Molecular Cloning: A Laboratory Manual", Cold Spring Harbor Laboratory Press; Ausubel et al, (1995), "Short Protocols in Molecular Biology", John Wiley and Sons; Methods in Enzymology (several volumes); Methods in Cell Biology (several volumes), and Methods in Molecular Biology (several volumes).

Pharmaceutically acceptable salts of the compounds disclosed herein can be used to practice the present invention. As used herein, a "pharmaceutically acceptable salt" of the disclosed compound is an ionic bond-containing product of reacting a compound of the invention with either an acid or a base, suitable for administering to a subject. For example, an acid salt of a compound containing an amine or other basic group can be obtained by reacting the compound with a suitable organic or inorganic acid, such as hydrogen chloride, hydrogen bromide, acetic acid, perchloric acid and the like. Other examples of such salts include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid. Salts can also be formed with suitable organic bases when the compound comprises an acid functional group such as —COOH or —$SO_3H$. Such bases suitable for the formation of a pharmaceutically acceptable base addition salts with compounds of the present invention include organic bases that are nontoxic and strong enough to react with the acid functional group. Such organic bases are well known in the art and include amino acids such as arginine and lysine, mono-, di-, and triethanolamine, choline, mono-, di-, and trialkylamine, such as methyl amine, dimethylamine, and trimethylamine, guanidine, N-benzylphenethylamine, N-methylglucosamine, N-methylpiperazine, morpholine, ethylendiamine, tris(hydroxymethyl)aminomethane and the like.

As used herein, a "pharmaceutical composition" is a formulation comprising the disclosed compounds and a pharmaceutically acceptable diluent or carrier, in a form suitable for administration to a subject. The pharmaceutical composition can be in bulk or in unit dosage form. The unit dosage form can be in any of a variety of forms, including, for example, a capsule, an IV bag, a tablet, a single pump on an aerosol inhaler, or a vial. The quantity of active ingredient (i.e., a formulation of the disclosed compound or salts thereof) in a unit dose of composition is an effective amount and may be varied according to the particular treatment involved. It may be appreciated that it may be necessary to make routine variations to the dosage depending on the age and condition of the patient. The dosage will also depend on the route of administration. A variety of routes are contemplated, including topical, oral, pulmonary, rectal, vaginal, parenteral, including transdermal, subcutaneous, intravenous, intramuscular, intraperitoneal and intranasal.

The compounds described herein, and the pharmaceutically acceptable salts thereof can be used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein. Techniques for formulation and administration of the compounds of the instant invention can be found in *Remington: the Science and Practice of Pharmacy*, 19$^{th}$ edition, Mack Publishing Co., Easton, Pa. (1995).

As used herein, a "subject" includes mammals, e.g., humans, companion animals (e.g., dogs, cats, birds and the like), farm animals (e.g., cows, sheep, pigs, horses, fowl and the like) and laboratory animals (e.g., rats, mice, guinea pigs and the like). In a preferred embodiment of the disclosed methods, the subject is human.

As used herein, a "therapeutically effective amount" of a compound of the disclosed invention is the quantity which, when administered to a subject in need of treatment, improves the prognosis of the subject, e.g., delays the onset of and/or reduces the severity of one or more of the subject's symptoms associated with a fungal infection. The amount of the disclosed compound to be administered to a subject will depend on the particular disease, the mode of administration, and the characteristics of the subject, such as general health, other diseases, age, sex, genotype, body weight and tolerance to drugs. The skilled artisan will be able to determine appropriate dosages depending on these and other factors. Effective amounts of the disclosed compounds typically range between about 0.1 mg/kg body weight per day and about 1000 mg/kg body weight per day, and preferably between 1 mg/kg body weight per day and 100 mg/kg body weight per day.

The present invention is based on the identification of the α-bungarotoxin sensitive receptor that, when exposed to an agonist of that receptor, inhibits the release of proinflammatory cytokines from macrophages when the macrophages are otherwise stimulated to release inflammatory cytokines. The receptor responsible for this inhibition is the α7 receptor. Thus, treatment of a macrophage with an agonist to the α7 receptor inhibits the macrophage from releasing proinflammatory cytokines, particularly TNF, if the macrophage was otherwise stimulated, e.g., with bacterial lipopolysaccharide (LPS), to release the proinflammatory cytokines.

Accordingly, in some embodiments the present invention is directed to methods of inhibiting the release of a proinflammatory cytokine from a mammalian cell. The methods comprise treating the cell with a cholinergic agonist in an amount sufficient to decrease the amount of the proinflammatory cytokine released from the cell, wherein the cholinergic agonist is selective for an α7 nicotinic receptor.

As used herein, a cytokine is a soluble protein or peptide which is naturally produced by mammalian cells and which act in vivo as humoral regulators at micro- to picomolar concentrations. Cytokines can, either under normal or pathological conditions, modulate the functional activities of individual cells and tissues. A proinflammatory cytokine is a cytokine that is capable of causing any of the following physiological reactions associated with inflammation: vasodialation, hyperemia, increased permeability of vessels with associated edema, accumulation of granulocytes and mononuclear phagocytes, or deposition of fibrin. In some cases, the proinflammatory cytokine can also cause apoptosis, such as in chronic heart failure, where TNF has been shown to stimulate cardiomyocyte apoptosis (Pulkki, 1997; Tsutsui et al., 2000). Nonlimiting examples of proinflammatory cytokines are tumor necrosis factor (TNF), interleukin (IL)-1α, IL-1β, IL-6, IL-8, IL-18, interferonγ, HMG-1, platelet-activating factor (PAF), and macrophage migration inhibitory factor (MIF). In preferred embodiments of the invention, the proinflammatory cytokine that is inhibited by cholinergic agonist treatment is TNF, an IL-1, IL-6 or IL-18, because these cytokines are produced by macrophages and mediate deleterious conditions for many important disorders, for example endotoxic shock, asthma, rheumatoid arthritis, inflammatory bile disease, heart failure, and allograft rejection. In most preferred embodiments, the proinflammatory cytokine is TNF.

Proinflammatory cytokines are to be distinguished from anti-inflammatory cytokines, such as IL-4, IL-10, and IL-13, which are not mediators of inflammation. In preferred embodiments, release of anti-inflammatory cytokines is not inhibited by cholinergic agonists.

In many instances, proinflammatory cytokines are produced in an inflammatory cytokine cascade, defined herein as an in vivo release of at least one proinflammatory cytokine in a mammal, wherein the cytokine release affects a physiological condition of the mammal. Thus, an inflammatory cytokine cascade is inhibited in embodiments of the invention where proinflammatory cytokine release causes a deleterious physiological condition.

Any mammalian cell that produces proinflammatory cytokines are useful for the practice of the invention. Nonlimiting examples are monocytes, macrophages, mast cells, neutrophils, epithelial cells, osteoblasts, fibroblasts, smooth muscle cells, and neurons. In preferred embodiments, the cell is a macrophage.

As used herein, an "α7 cholinergic receptor" is a receptor comprising an α7 subunit. The receptor can comprise only α7 subunits; alternatively the receptor comprises α7 subunit(s) and subunit(s) from other cholinergic receptor subtypes. In one embodiment, the receptor is a homopentamer. In another embodiment, the receptor is a heteropentamer.

As used herein, an "α7 cholinergic receptor agonist" is a compound that binds to a receptor comprising an α7 subunit, in vivo or in vitro, inducing the receptor to perform its physiological function. In one embodiment, a cholinergic receptor agonist inhibits release of proinflammatory cytokines from cells expressing cholinergic receptors comprising α7 subunits when the cell is otherwise stimulated to release those proinflammatory cytokines. The skilled artisan can determine whether any particular compound is an α7 receptor agonist by any of several well known methods, for example those provided in the Example 1 below.

When referring to the effect of the cholinergic agonist on release of proinflammatory cytokines or an inflammatory cytokine cascade, or the effect of vagus nerve stimulation on an inflammatory cytokine cascade, the use of the terms "inhibit" or "decrease" encompasses at least a small but measurable reduction in proinflammatory cytokine release. In preferred embodiments, the release of the proinflammatory cytokine is inhibited by at least 20% over non-treated controls; in more preferred embodiments, the inhibition is at least 50%; in still more preferred embodiments, the inhibition is at least 70%, and in the most preferred embodiments, the inhibition is at least 80%. Such reductions in proinflammatory cytokine release are capable of reducing the deleterious effects of an inflammatory cytokine cascade in in vivo embodiments.

Any α7 agonist, now known or later discovered, would be expected to inhibit the release of proinflammatory cytokines from mammalian cells. In preferred embodiments, the cholinergic agonist is not otherwise toxic to the cell at useful concentrations. In more preferred embodiments, the cholinergic agonist has been used therapeutically in vivo or is naturally produced by mammalian cells. Nonlimiting examples include acetylcholine, muscarine, nicotine, 3-2,4-dimethoxybenzylidine anabaseine (DMXB-A, also known as GTS-21) (Kem et al., 1997; Simosky et al., 2001), choline, cocaine methiodide (Francis et al., 2001).

In most preferred embodiments, the cholinergic agonist is an agonist that is selective or specific for α7, since such an agonist would be expected to cause fewer side effects than a non-specific cholinergic agonist (e.g., nicotine), to a subject that is being treated for inflammation. As used herein, an agonist is selective for α7 if that agonist is an agonist that activates α7 to a greater extent than the agonist activates at least one other nicotinic receptor. Such an activation difference can be measured by comparing activation of the various receptors by any known method, for example using an in vitro receptor binding assay, such as those produced by NovaScreen Biosciences Corporation (Hanover, Md.), or by the methods disclosed in WO 02/44176 (α4β2 tested), U.S. Pat. No. 6,407,095 (peripheral nicotinic receptor of the ganglion type), U.S. Patent Application Publication No. 2002/0086871 (binding of labeled ligand to membranes prepared from GH$_4$C1 cells transfected with the receptor if interest), U.S. Patent Application Publication No. 2002/0086871 (α1 and α4), and WO 97/30998. References which describe methods of determining agonists that are selective for α7 receptors include: U.S. Pat. No. 5,977,144 (Table 1), WO 02/057275 (p 41-42) and Holladay et al. (1997). The teachings of these references are incorporated herein by reference. Assays for other nicotinic receptor subtypes are known to the skill artisan.

In a preferred method, the binding or activity (current responses) of *Xenopus oocytes* expressing either the α7 receptor subtype or another receptor subtype (e.g., α4β2) after administration of the agonist. Agonists that result in greater activation of the α7 receptor subtype are determined to be α7 selective agonists. Using any of the above methods or an equivalent method, it is preferred that the selective α7 agonist is at least two-fold, more preferably at least five-fold, even more preferably at least 10-fold, and most preferably at least 50-fold more able to activate the α7 receptor than at least one other nicotinic receptor.

An agonist is specific for α7 if that agonist activates the α7 receptor to a much greater degree (i.e., at least 10-fold, preferably at least 20-fold, more preferably at least 50-fold) than any other nicotinic receptor. Most preferably, the specific agonist will not activate another nicotinic receptor to any measurable degree (i.e., significant at P=0.05 vs. untreated receptor in a well-controlled comparison). Non-limiting examples of specific α7 agonists are DMXB-A (Compound (V)) and cocaine methiodide.

In some embodiments the nicotinic cholinergic agonist is a compound of formula I:

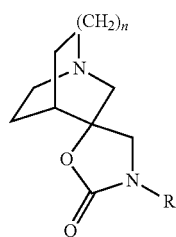

wherein, R represents hydrogen or methyl, and
n represents 0 or 1;
or a pharmaceutically acceptable salt thereof. In particularly preferred embodiments the nicotinic cholinergic agonist is (−)-spiro[1-azabicyclo[2.2.2]octane-3,5'-oxazolidin-2'-one] (Compound (VII)). Methods of preparation of compounds of formula I are described in U.S. Pat. No. 5,902,814, the teachings of which are incorporated herein by reference in their entirety.

In other embodiments the nicotinic cholinergic agonist is a compound of formula II:

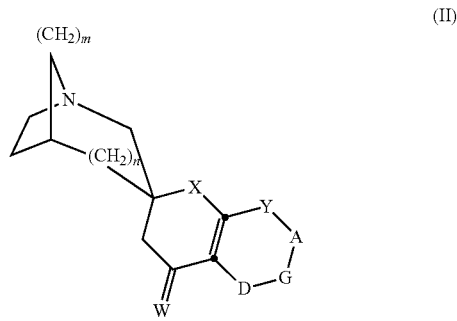

wherein:
m is 1 or 2;
n is 0 or 1;
Y is CH, N or NO;
X is oxygen or sulfur;
W is oxygen, H$_2$ or F$_2$;
A is N or C(R$^2$);
G is N or C(R$^3$);
D is N or C(R$^4$);
with the proviso that no more than one of A, G and D is nitrogen but at least one of Y, A, G and D is nitrogen or NO;
R$^1$ is hydrogen or C$_1$-C$_4$ alkyl;
R$^2$, R$^3$ and R$^4$ are independently hydrogen, halogen, C$_1$-C$_4$ alkyl, C$_2$-C$_4$ alkenyl, C$_2$-C$_4$ alkynyl, aryl, heteroaryl, OH, OC$_1$-C$_4$ alkyl, CO$_2$R$_1$, —CN, —NO$_2$, —NR$_5$R$_6$, —CF$_3$ or —OSO$_2$CF$_3$, or R$^2$ and R$^3$, R$^3$ and R$^4$, respectively, may together form another six membered aromatic or hetero aromatic ring sharing A and G, or G and D, respectively, containing between zero and two nitrogen atoms, and substituted with one to two of the following substitutents: independently hydrogen, halogen, C$_1$-C$_4$ alkyl, C$_2$-C$_4$ alkenyl, C$_2$-C$_4$ alkynyl, aryl, heteroaryl, OH, OC$_1$-C$_4$ alkyl, CO$_2$R$^1$, —CN, —NO$_2$, —NR$^5$R$^6$, —CF$_3$ or —OSO$_2$CF$_3$;
R$^5$ and R$^6$ are independently hydrogen, C$_1$-C$_4$ alkyl, C(O)R$^7$, C(O)NHR$^8$, C(O)OR$^9$, SO$_2$R$^{10}$ or may together be (CH$_2$)$_j$Q(CH$_2$)$_k$ where Q is O, S, NR$^{11}$,
or a bond;
j is 2 to 7;
k is 0 to 2;
R$^7$, R$^8$, R$^9$, R$^{10}$ and R$^{11}$ are independently C$_1$-C$_4$ alkyl, aryl, or hetero aryl, or
an enantiomer thereof;
or a pharmaceutically acceptable salts thereof. In preferred embodiments, a cholinergic agonist is a compound of formula II wherein m is 1; n is 0; p is 0; x is oxygen; A is C(R$^2$); G is C(R$^3$); and D is C(R$^4$). In a particularly preferred embodiment the nicotinic cholinergic agonist is (R)-(−)-5'-phenylspiro[1-azabicyclo[2.2.2]octane-3,2'-(3'H)-furo[2,3-b]pyridine]. Methods of preparation of compounds of formula II are described in U.S. Pat. No. 6,110,914, the teachings of which are incorporated herein by reference in their entirety.

In additional embodiments the nicotinic cholinergic agonist is a compound of formula III:

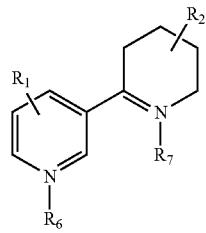

wherein $R_1$, $R_6$ and $R_7$ are hydrogen or $C_1$-$C_4$ alkyl; and $R_2$ is selected from a group of

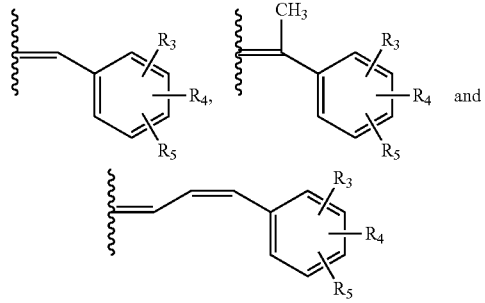

wherein, $R_3$, $R_4$ and $R_5$ are selected from the group consisting of hydrogen, $C_1$-$C_4$ alkyl optionally substituted with N,N-dialkylamino having 1 to 4 carbons in each of the alkyls, $C_1$-$C_6$ alkoxy optionally substituted with N,N-dialkylamino having 1 to 4 carbons in each of the alkyls, carboalkoxy having 1 to 4 carbons in the alkoxy, amino, amido having 1 to 4 carbons in the acyl, cyano, and N,N-dialkylamino having 1 to 4 carbons in each of the alkyls, halo, hydroxyl or nitro.

In a preferred embodiment, an agonist is a compound of formula III, wherein $R_2$ is attached to the 3-position of the tetrahydropyridine ring, and further wherein $R_3$, which is attached to the 4- or the 2-position of the phenyl ring, is selected from the group consisting of amino, hydroxyl, chloro, cyano, dimethylamino, methyl, methoxy, acetylamino, acetoxy, and nitro. In one particularly preferred embodiment, the agonist is a compound of formula III, wherein $R_3$ is hydroxyl, and wherein $R_1$, $R_4$, and $R_5$ are hydrogen. In another particularly preferred embodiment, the agonist is a compound of formula III, wherein $R_3$ is acetylamino and wherein $R_1$, $R_4$, and $R_5$ are hydrogen. In another particularly preferred embodiment, the agonist is a compound of formula III, wherein $R_3$ is acetoxy and wherein $R_1$, $R_4$, and $R_5$ are hydrogen. In another particularly preferred embodiment, the agonist is a compound of formula III, wherein $R_3$ is methoxy, and wherein $R_1$, $R_4$, and $R_5$ are hydrogen. In yet another particularly preferred embodiment, the agonist is a compound of formula III, wherein $R_3$ is methoxy and wherein $R_1$ and $R_4$ are hydrogen, and further wherein $R_3$ is attached to the 2-position of the phenyl ring, and $R_5$, which is attached to the 4-position of the phenyl ring, is methoxy or hydroxy. In particularly preferred embodiments the nicotinic cholinergic agonist is selected from the group consisting of 3-2,4-dimethoxybenzylidine anabaseine (DMXB-A; Compound (V)), 3-(4-hydroxybenzylidene)anabaseine, 3-(4-methoxybenzylidene)anabaseine, 3-(4-aminobenzylidene)anabaseine, 3-(4-hydroxy-2-methoxybenzylidene)anabaseine (Compound (VI)), 3-(4-methoxy-2-hydroxybenzylidene)anabaseine, trans-3-cinnamylidene anabaseine, trans-3-(2-methoxycinnamylidene)anabaseine and trans-3-(4-methoxycinnamylidene)anabaseine. Methods of preparation of compounds of formula III are described in U.S. Pat. No. 5,977,144, the teachings of which are incorporated herein by reference in their entirety.

In further embodiments the agonist is a compound of formula IV:

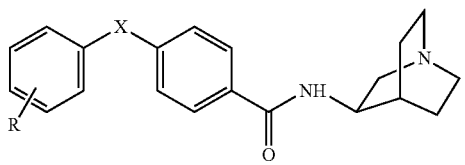

wherein X is O or S; and

R is selected from the group consisting of H, $OR_1$, $NHC(O)R_1$, and a halogen, wherein $R_1$ is a hydrogen or a $C_1$-$C_4$ alkyl. In a particularly preferred embodiment the nicotinic cholinergic agonist is selected from a group consisting of N-[(3R)-1-azabicyclo[2.2.2]oct-3-yl]-4-(4-hydroxyphenoxyl)benzamide, N-[(3R)-1-azabicyclo[2.2.2]oct-3-yl]-4-(4-acetamidophenoxyl)benzamide, N-[(3R)-1-azabicyclo[2.2.2]oct-3-yl]-4-(phenylsulfanyl)benzamide, and N-[(3R)-1-azabicyclo[2.2.2]oct-3-yl]-4-(3-chlorophenylsulphonyl)benzamide. Methods of preparation of compounds of formula IV have are described in PCT Patent Application Publication WO 01/85727, the teachings of which are incorporated herein by reference in their entirety.

In yet other embodiments, the agonist is (1-aza-bicyclo[2.2.2]oct-3-yl)-carbamic acid 1-(2-fluorophenyl)-ethyl ester. Methods of preparation of this compound have been described in U.S. Patent Application Publication 2002/0040035, the teachings of which are incorporated herein by reference in their entirety.

In still other embodiments, the α7 agonist is an antibody which is a selective agonist (most preferably a specific agonist) of the α7 nicotinic receptor. The antibodies can be polyclonal or monoclonal; may be from any of a number of human, non-human eukaryotic, cellular, fungal or bacterial sources; may be encoded by genomic or vector-borne coding sequences; and may be elicited against native or recombinant α7 or fragments thereof with or without the use of adjuvants, all according to a variety of methods and procedures well-known in the art for generating and producing antibodies. Other examples of such useful antibodies include but are not limited to chimeric, single-chain, and various human or humanized types of antibodies, as well as various fragments thereof such as Fab fragments and fragments produced from specialized expression systems.

The present invention is also directed to antibodies which are α7 agonists, as described above.

A nonlimiting example of methods for generating antibodies for the α7 nicotinic receptor is immunizing a suitable laboratory animal with the α7 receptor or a fragment thereof and isolating the antibodies elicited by the immunization which bind α7. Immunization and isolation procedures are well known to one of ordinary skill in the art. Antibodies which are agonists can be identified by the procedures disclosed herein, for example, by combining the isolated antibodies with a macrophage that has been stimulated to release proinflammatory cytokine, or any other suitable method for assessing α7 receptor activity. Inhibition of cytokine release is indicative of the agonist activity. Selectivity for α7 can be assessed by screening for activity against at least one other nicotinic or cholinergic receptor, as previously discussed. Antibodies that are found to be selective agonist for the α7 receptor may be further evaluated for their efficacy in treating one or more of the inflammatory diseases described herein, e.g., additional iii. vitro tests or in vivo tests in animal models. The present invention also includes α7 selective antibody agonists identified by this method.

The present invention is useful for studying cells in culture, for example studying the effect of inflammatory cytokine release on the biology of macrophages, or for testing compounds for cholinergic agonist activity. However, in vivo applications make up many of the preferred embodiments. In those embodiments, the cell is in a patient suffering from, or at risk for, a condition mediated by an inflammatory cytokine cascade. As used herein, a patient can be any mammal. However, in preferred embodiments, the patient is a human.

Thus, in some embodiments, the invention is directed to methods of inhibiting an inflammatory cytokine cascade in a patient. The methods comprise treating the patient with a cholinergic agonist in an amount sufficient to inhibit the inflammatory cytokine cascade, wherein the patient is suffering from, or at risk for, a condition mediated by the inflammatory cytokine cascade. Preferably, the cholinergic agonist is selective for an α7 nicotinic receptor.

The treatment of any condition mediated by an inflammatory cytokine cascade is within the scope of the invention. In preferred embodiments, the condition is one where the inflammatory cytokine cascade is affected through release of proinflammatory cytokines from a macrophage. The condition can be one where the inflammatory cytokine cascade causes a systemic reaction, such as with septic shock. Alternatively, the condition can be mediated by a localized inflammatory cytokine cascade, as in rheumatoid arthritis.

Nonlimiting examples of conditions which can be usefully treated using the present invention include those conditions enumerated in the background section of this specification. Preferably, the condition is appendicitis, peptic, gastric or duodenal ulcers, peritonitis, pancreatitis, acute or ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopic silicovolcanoconiosis, alvealitis, bronchiolitis, pharyngitis, pleurisy, sinusitis, influenza, respiratory syncytial virus, herpes, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcet's syndrome, allograft rejection, graft-versus-host disease, Type I diabetes, ankylosing spondylitis, Berger's disease, Type II diabetes, ankylosing spondylitis, Berger's disease, Retier's syndrome, or Hodgkins disease.

In an alternative embodiment, the condition is any of the conditioned listed above, provided that the condition is not ulcerative colitis, stroke, Type II diabetes, Crohn's disease, Alzheimer's disease or an inflammatory skin condition.

In one embodiment, the condition is appendicitis, peptic, gastric or duodenal ulcers, peritonitis, pancreatitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection or graft-versus-host disease.

In another embodiment, the condition is appendicitis, peptic, gastric or duodenal ulcers, peritonitis, pancreatitis, hepatitis, asthma, allergy, anaphylactic shock, organ ischemia, reperfusion injury, organ necrosis, hay fever, sepsis, septicemia, endotoxic shock, cachexia, septic abortion, disseminated bacteremia, burns, congestive heart failure, adult respiratory distress syndrome, cerebral infarction, cerebral embolism, spinal cord injury, paralysis, allograft rejection or graft-versus-host disease. In one embodiment, the condition is sepsis.

In yet another embodiment, the condition is selected from the group consisting of peritonitis, pancreatitis, organ ischemia, reperfusion injury, sepsis, endotoxic shock, cachexia, burns, adult respiratory distress syndrome, chronic obstructive pulmonary disease, psoriasis, rheumatoid arthritis, systemic lupus erythematosis, myocardial ischemia, and allograft rejection.

In an alternative embodiment, the condition is selected from the group consisting of peritonitis, pancreatitis, sepsis, endotoxic shock, adult respiratory distress syndrome, chronic obstructive pulmonary disease, rheumatoid arthritis, systemic lupus erythematosis, myocardial ischemia, allograft rejection, asthma, graft-versus-host-disease, congestive heart failure and cystic fibrosis.

These conditions are preferably treated with any of Compounds I-VII or pharmaceutically acceptable salts thereof.

The route of administration of the cholinergic agonist depends on the condition to be treated. For example, intravenous injection may be preferred for treatment of a systemic disorder such as septic shock, and oral administration may be preferred to treat a gastrointestinal disorder such as a gastric ulcer. The route of administration and the dosage of the cholinergic agonist to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. Thus, depending on the condition, the cholinergic agonist can be administered orally, parenterally, intranasally, vaginally, rectally, lingually, sublingually, bucally, intrabuccaly and transdermally to the patient.

Accordingly, cholinergic agonist compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

Cholinergic agonist compositions of the present invention can easily be administered parenterally such as for example, by intravenous, intramuscular, intrathecal or subcutaneous injection. Parenteral administration can be accomplished by incorporating the cholinergic agonist compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfate and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the cholinergic agonist in the glycerin, mixing the heated glycerin after which purified water may be added, and pouring the hot mixture into a suppository mold.

Transdermal administration includes percutaneous absorption of the cholinergic agonist through the skin. Transdermal formulations include patches (such as the well-known nicotine patch), ointments, creams, gels, salves and the like.

The present invention includes nasally administering to the mammal a therapeutically effective amount of the cholinergic agonist. As used herein, nasally administering or nasal administration includes administering the cholinergic agonist to the mucous membranes of the nasal passage or nasal cavity of the patient. As used herein, pharmaceutical compositions for nasal administration of a cholinergic agonist include therapeutically effective amounts of the agonist prepared by well-known methods to be administered, for example, as a nasal spray, nasal drop, suspension, gel, ointment, cream or powder. Administration of the cholinergic agonist may also take place using a nasal tampon or nasal sponge.

As previously discussed, the preferred cholinergic agonists for these methods are selective or specific for the $\alpha 7$ receptor, including for example DMXB-A (Compound (V)), cocaine methiodide.

The present invention is also directed to methods for determining whether a compound is a cholinergic agonist reactive with an $\alpha 7$ nicotinic receptor. The methods comprise determining whether the compound inhibits release of a proinflammatory cytokine from a mammalian cell. In these methods, a compound that inhibits the release of the proinflammatory cytokine from the mammalian cell is a cholinergic agonist reactive with an $\alpha 7$ nicotinic receptor.

These methods preferably involve treating the mammalian cell with the compound along with an agent that stimulates a proinflammatory cytokine cascade. A preferred agent is bacterial lipopolysaccharide (LPS). The compound can be administered to the mammalian cell either before the agent, at the same time as the agent, or after the agent. Preferably, the compound is administered before the agent. See, e.g., U.S. patent application Ser. No. 09/855,446.

In preferred embodiments, compounds that are determined to be $\alpha 7$ agonists are further tested for the ability to activate at least one other nicotinic receptor subtype, in order to determine whether the $\alpha 7$ agonist is selective or specific. Test compounds which selectively or specifically activate the $\alpha 7$ subtype can be further subjected to more advanced testing, e.g., further in vitro testing or in vivo testing in animal models to further assess the compounds suitability for treating subjects with inflammatory disorders.

These methods are not narrowly limited to any particular compound to be tested. Although most cholinergic agonists now known are small molecules, $\alpha 7$ agonist activity could be present in a protein (e.g., an antibody, as previously discussed), an oligonucleotide or mimetic (e.g., an aptamer) or any other compound. These methods are suitable for testing any of those potential $\alpha 7$ agonists.

For these methods, the cell can be any cell that can be induced to produce a proinflammatory cytokine. In preferred embodiments, the cell is an immune cell, for example macrophages, monocytes, or neutrophils. In the most preferred embodiments, the cell is a macrophage.

The proinflammatory cytokine to be measured for inhibition can be any proinflammatory cytokine that can be induced to be released from the cell. In preferred embodiments, the cytokine is TNF.

Evaluation of the inhibition of cytokine production can be by any means known, including quantitation of the cytokine (e.g., with ELISA), or by bioassay, (e.g. determining whether proinflammatory cytokine activity is reduced), or by measurement of the proinflammatory cytokine mRNA. The skilled artisan could utilize any of these assays without undue experimentation. See also U.S. patent application Ser. No. 09/855,446 for examples of several assays useful in this regard.

These methods can be performed in vivo, where an animal, e.g., a rat, is treated with the compound along with an agent that stimulates a proinflammatory cytokine cascade, and the effect of the agent on induction of the proinflammatory cytokine cascade is measured, e.g., by measuring serum TNF levels. However, due to the relative ease of doing these types of assays with cells culture rather than with whole animals, the methods are preferably performed in vitro, for example using macrophage cultures.

In related embodiments, the invention is directed to methods for determining whether a compound is a cholinergic antagonist reactive with an α7 nicotinic receptor. These methods comprise determining whether the compound reduces the ability of a cholinergic agonist to inhibit the release of a proinflammatory cytokine from a mammalian cell. In these embodiments, a compound, that reduces the ability of a cholinergic agonist to inhibit the release of a proinflammatory cytokine from a mammalian cell is a cholinergic antagonist reactive with an α7 receptor.

These methods preferably involve treating the mammalian cell with the compound along with an α7 agonist and an agent that stimulates a proinflammatory cytokine cascade. Thus, these methods are essentially like the methods described immediately above, except the compound of the previous assay is an α7 agonist that inhibits the proinflammatory cytokine release from the cell that is otherwise induced by the agent. The test compound is evaluated to determine whether it can prevent the α7 agonist from inhibiting the proinflammatory cytokine cascade caused by the agent (e.g., LPS). The cells and agent can be as described for the immediately preceding methods; the α7 agonist can be any non-specific, selective, or specific α7 agonist known, e.g., nicotine or DMXB-A. Also as with the immediately preceding methods, these methods can be performed in vivo but are preferably performed in vitro.

As with the immediately preceding method, the compound being tested for α7 antagonistic activity is not limited to small molecular weight compounds, but could include any compound, including proteins, oligopeptides, or oligopeptide mimetics. Also as with the immediately preceding method, evaluation of the efficacy of the test compound, by measuring inhibition of cytokine production, can be by any means known, including quantitation of the cytokine (e.g., with ELISA), or by bioassay, (e.g. determining whether proinflammatory cytokine activity is reduced), or by measurement of the proinflammatory cytokine mRNA. The skilled artisan could utilize any of these assays without undue experimentation.

In other embodiments, the invention is directed to methods for determining whether a test compound has the ability to inhibit inflammation. In some aspects, these methods comprise determining whether the test compound is a cholinergic agonist reactive with an α7 nicotinic receptor. Preferably the methods further comprise determining whether the test compound is selective for α7 by testing the test compound for its ability to activate at least one other nicotinic receptor. These determinations can be made as previously described, e.g., by determining whether the compound inhibits release of a proinflammatory cytokine from a mammalian cell, preferably a macrophage.

In other aspects, the methods for determining whether a test compound has the ability to inhibit inflammation comprise determining whether the test compound inhibits binding of an antagonist to an α7 nicotinic receptor, for example by determining whether the test compound inhibits binding of FITC-α-bungarotoxin from a macrophage. See Example 1, where in some embodiments the method would utilize the α-bungarotoxin staining and confocal microscopy method, except the test compound would be added to determine whether the compound would inhibit binding of the α-bungarotoxin to the macrophages.

In some cases it may be desirable to restrict the ability of a mammalian cell to inhibit proinflammatory cytokine release. Examples of such cases are when proinflammatory cytokines are desired to prevent or fight cancer, or when the physiological effects of the α7 receptor is being studied. The present invention is thus also directed to methods of inhibiting attenuation of release of a proinflammatory cytokine from a mammalian cell upon exposure of the cell to a cholinergic agonist. The methods comprise treating the cell with an agent that inhibits binding of the cholinergic agonist to an α7 receptor. As with previously described methods, the preferred cell for these methods is a macrophage.

The skilled artisan could envision several ways that the binding of the cholinergic agonist to the α7 receptor on a cell could be inhibited. Examples include treatment of the cell with an α7 antagonist; treating the cell with an antibody or aptamer that binds to the α7 receptor, preventing binding of the cholinergic agonist to the receptor; or, preferably, treating the cell with an antisense oligonucleotide or mimetic that is complementary to the α7 mRNA and capable of inhibiting translation of the mRNA to the α7 receptor. See Example 1 for evidence of the effectiveness of such an antisense mimetic. As used herein, a mimetic is an oligonucleotide analog that differs chemically from a naturally occurring oligonucleotide, but that is capable of oligonucleotide-like noncovalent binding to a complementary nucleotide sequence. See, e.g., U.S. Pat. No. 6,436,909 for a discussion of useful mimetics. In preferred embodiments, the agent is a phosphorothionate oligonucleotide mimetic, complementary to the relevant a'7 gene. The α7 gene is provided, e.g., in Peng et al., 1994. An example of a useful antisense sequence is 5'-gcagcgcatgttgagtcccg-3' (see Example 1) or a similar sequence, preferably surrounding the translation initiation codon of the human α7 subunit gene.

Thus, the invention is also directed to oligonucleotides or mimetics capable of inhibiting attenuation of lipopolysaccharide-induced TNF release from a mammalian macrophage upon exposure of the macrophage to a cholinergic agonist. The oligonucleotides or mimetics comprise a sequence greater than 5 nucleotides long that is complementary to an mRNA of an α7 receptor. Preferably, the oligonucleotides or mimetics are complementary to the transcription initiation region of the α7 mRNA. Most preferably, the oligonucleotide or mimetic comprises the sequence 5'-gcagcgcatgttgagtcccg-3'.

Preferred embodiments of the invention are described in the following Examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the Example.

Example 1

α7 Nicotinic Receptor as the Molecular Substrate of Neuro-Immune Synapse

Example Summary

Here we report that the nicotinic receptor α7 subunit is required for acetylcholine inhibition of macrophage TNF release. α-bungarotoxin bound to discrete receptor clusters expressed on the surface of primary human macrophages. Immunoblotting with α7-specific antibodies confirmed identity of the α7 subunit in proteins isolated by adherence to α-bungarotoxin-conjugated beads. Exposure of macrophages to α7 antisense oligonucleotides decreased α-bungarotoxin binding and restored TNF release in the presence of nicotine. Mice deficient in the nicotinic receptor α7 subunit produced significantly more TNF, IL-1β and IL-6 during endotoxemia, as compared to wild type mice. Macrophages isolated from α7 knockout mice failed to respond to cholinergic agonists, and continued to produce TNF. Finally, electrical stimulation of the vagus nerve using a protocol that inhibited TNT release in wild-type mice did not inhibit TNF release in α7-deficient mice. Thus, the nicotinic acetylcholine receptor α7 subunit is essential for cholinergic inhibition of proinflammatory cytokines.

Results and Discussion

As a first step in identifying the macrophage receptor involved in inhibition of proinflammatory cytokine release, primary human macrophages were labeled with FITC-α-bungarotoxin, a peptide antagonist that binds to a subset of cholinergic receptors (Lindstrom, 1995; Leonard & Bertrand, 2001). Strong binding of α-bungarotoxin was observed on the macrophage surface (FIG. 1a). Nicotine pretreatment markedly reduced the intensity of binding (FIG. 1b). At neuro-muscular junctions and the neuronal synapses, nicotinic receptors form receptor aggregates or clusters that facilitate fast signal transmission (Lin et al., 2001; Feng et al., 1998; Shoop et al., 2000). Discrete clusters of α-bungarotoxin binding can be clearly observed under higher magnification on the surface of macrophages, especially concentrated on the surface of the cell body (FIG. 1c, d).

To date, α1, α7 and α9 are the α-bungarotoxin-binding nicotinic receptor subunits known in human cells (Lindstrom, 1995; Leonard and Bertrand, 2001). a1 together with β1, δ and either ε (adult) or γ (fetal) subunits, forms heteropentameric nicotinic receptors that regulate muscle contraction; α7 and α9 can each form homopentameric nicotinic receptors (Lindstrom, 1995; Leonard and Bertrand, 2001). To determine if these receptor subunits are expressed in macrophages, we isolated RNA from primary human macrophages differentiated in vitro from peripheral blood mononuclear cells (PBMC) and performed RT-PCR analyses. To increase the sensitivity and specificity of the experiments, we conducted two rounds of PCR after reverse transcription, using nested primers specific to each subunit. The identities of the PCR products were confirmed by sequencing. The expression of both α1, α10, (data not shown) and α7 (FIG. 2a) mRNA was detected in human macrophages derived from unrelated blood donors. The same RT-PCR strategy did not detect the expression of α9 subunit mRNA in macrophages (data not shown).

Figure 2:
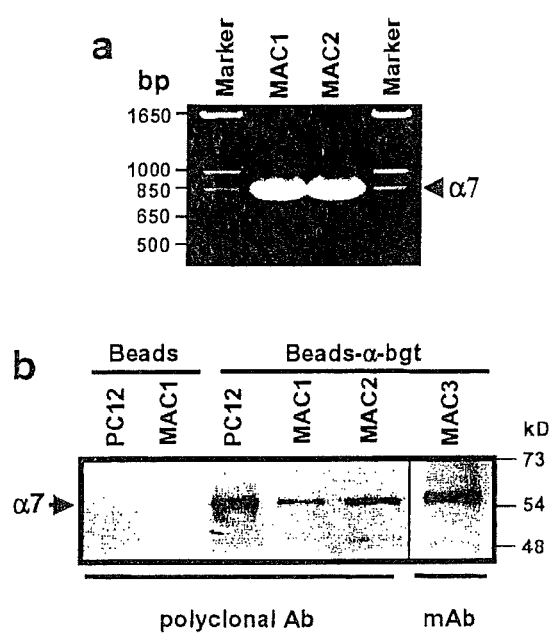
FIG. 2 are photographs of gels and western blots showing the mRNA and protein expression of α7 and α1 nicotinic receptors in primary human marophages. Panel a shows results of RT-PCR with α7-specific primers, generating a 843 bp α7 band. PCR products were verified by sequencing (data not shown). MAC1 and MAC2: macrophages derived from two unrelated donors. Panel b shows western blots. Cell lysates from PC12 cells or human macrophages (MAC) were incubated with either control Sepharose beads or Sepharose beads conjugated with α-bungarotoxin. The bound proteins were then analyzed by α7-specific polyclonal and monoclonal antibodies as indicated.

The protein expression of α1 and α7 subunits was next examined by western blotting. The α7 specific antibody recognized a clear band with an apparent molecular weight of about 55 kD (similar to the published molecular weight for α7 protein [Peng et al., 1994; Drisdel and Green, 2000]) from both differentiated primary macrophages and from undifferentiated PBMCs (data not shown). α1 protein expression was down-regulated to undetectable levels during in vitro differentiation of PBMC to macrophages (data not shown). The δ subunit, a necessary component of the α1 heteropentameric nicotinic acetylcholine receptor, could not be detected by this nested RT-PCR strategy (data not shown). To confirm that the positive signals in macrophages represented α7 nicotinic receptor that binds α-bungarotoxin, we used α-bungarotoxin-conjugated beads to pull-down proteins prepared from either human macrophages or PC12 cells (rat pheochromocytoma cells, which have been shown to express α7 homopentamer [Drisdel and Green, 2000]). Retained proteins were analyzed by western blotting using polyclonal or monoclonal α7 specific antibodies that recognized both human and rat α7 protein (the human and rat α7 proteins contain the same number of amino acids and are 94% identical [Peng et al., 1994; Seguela et al., 1993]). The results clearly showed that the human macrophages express α-bungarotoxin-binding α7 protein with apparent molecular weight that is similar to α7 subunit in PC12 cells (FIG. 2b). The identity of the macrophage α7 subunit was confirmed by cloning of the full-length macrophage-expressed α7 by RT-PCR methods. The full-length nicotinic acetylcholine α7 subunit in macrophages contains exons 1 to 10, identical to the nicotinic acetylcholine α7 subunit expressed in neurons (Gault et al., 1998). Together, these data identify the nicotinic acetylcholine α7 subunit as the α-bungarotoxin-binding receptor expressed on the surface of human macrophages.

Figure 3:
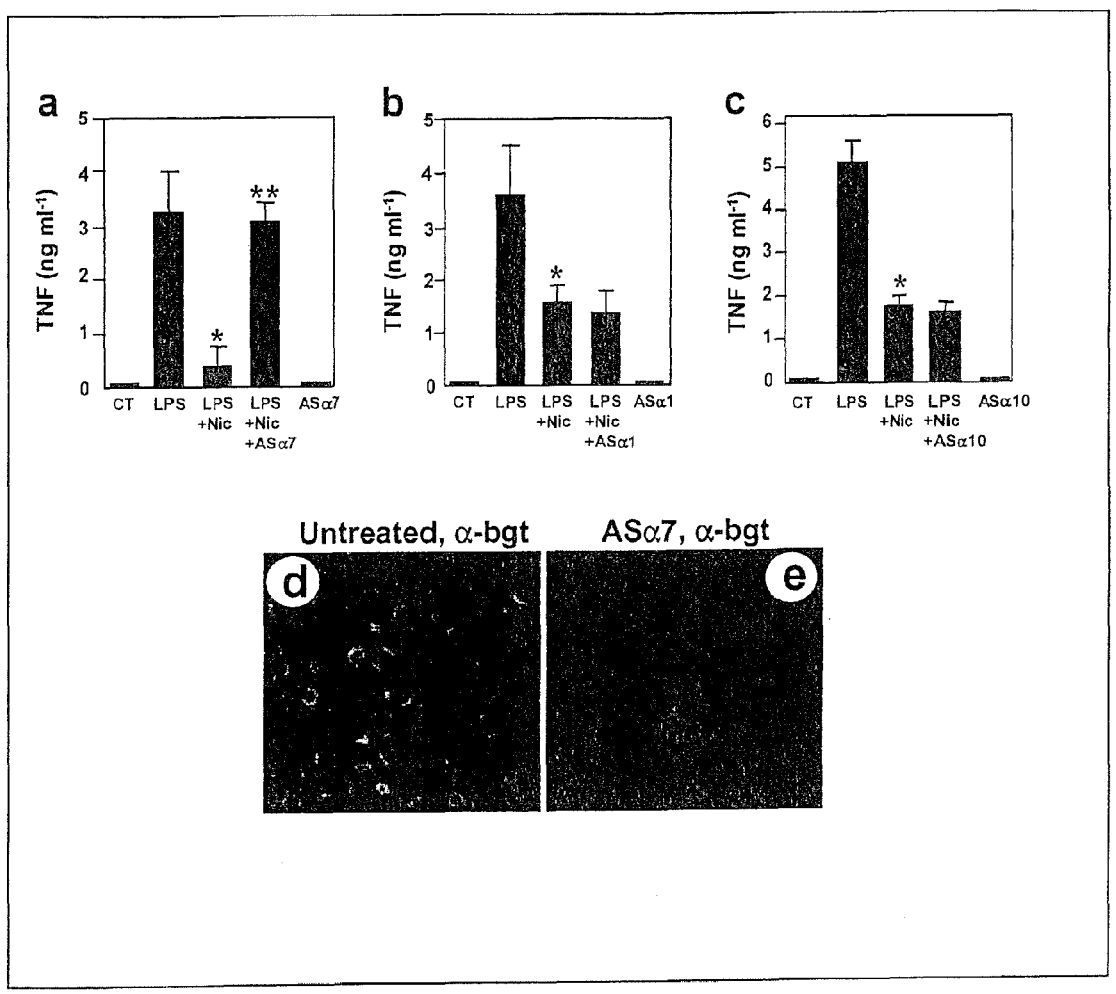
FIG. 3 shows graphs and micrographs establishing that antisense oligonucleotides to the α7 subunit of nicotinic acetylcholine receptors inhibits the effect of nicotine on TNF release. Panels a-c are graphs summarizing experimental results showing the LPS-stimulated TNF release from primary human macrophages pre-treated with antisense oligonucleotides to various subunits of nicotinic receptors. Where indicated, nicotine (Nic, 1 μM) was added 5-10 min before LPS induction (100 ng/ml). TNF levels in the cell culture medium were determined by L929 assays. CT: control (unstimulated) macrophage cultures. ASα7, ASα1 and ASα10: antisense oligonucleotides to α7, α1 and α10 subunits, respectively. Panels d and e are fluorescent micrographs showing FITC-α-bungarotoxin staining of primary human macrophages treated (e) or untreated (d) with the α7 antisense oligonucleotide (ASα7) and viewed by fluorescent confocal microscopy.

To study whether the α7 receptor is required for cholinergic inhibition of TNF release, we synthesized phosphorothioate antisense oligonucleotides surrounding the translation initiation codon of the human α7 subunit gene. Antisense oligonucleotides to similar regions of the α1 and α10 subunit genes were synthesized as controls. Macrophages exposed to the antisense oligonucleotides specific for α7 (ASα7) were significantly less responsive to the TNF-inhibitory action of nicotine (FIG. 3a). Antisense oligonucleotides to nicotinic acetylcholine α7 subunit restored macrophage TNF release in the presence of nicotine. Exposure of macrophages to ASα7 did not stimulate TNF synthesis in the absence of LPS and nicotine. Antisense oligonucleotides to α1 (ASα1) and α10 (ASα10) subunits, under similar conditions, did not significantly change the effect of nicotine on LPS-induced TNF release (FIG. 3b, c), indicating that the suppression of TNF by nicotine is specific to nicotinic acetylcholine receptor α7 subunit. Additional sets of antisense oligonucleotides to α7, α1 and α10 gave similar results (data not shown). Addition of the nicotinic acetylcholine α7 subunit antisense oligonucleotides to macrophage cultures decreased the surface binding of FITC-labeled α-bungarotoxin (FIG. 3d, e). Together these data indicate that the nicotinic acetylcholine receptor α7 subunit nicotinic receptor is necessary for cholinergic anti-inflammatory pathway dependent inhibition of TNF release in macrophages.

Figure 4:
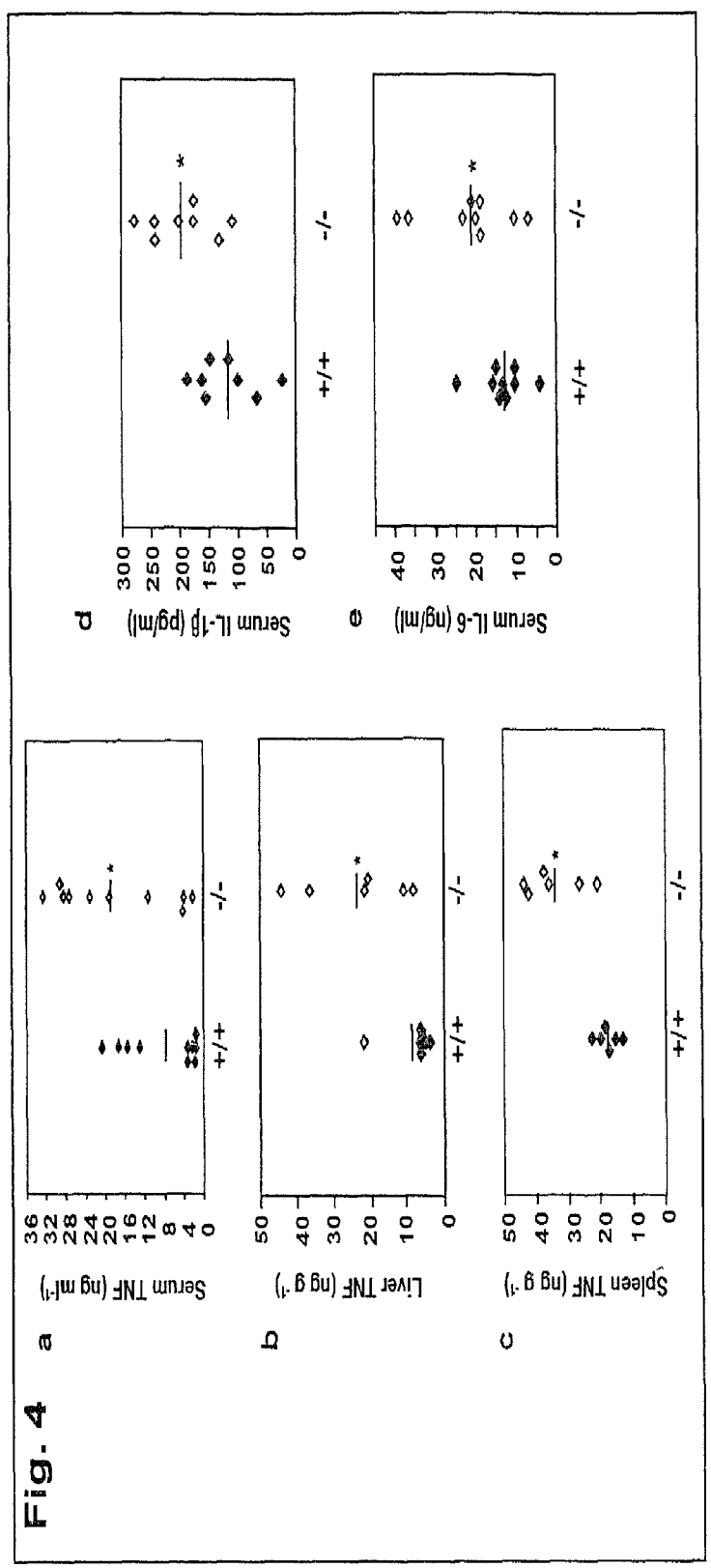
FIG. 4 is graphs summarizing experiments demonstrating increased cytokine production in α7-deficient mice during endotoxemia. α7 subunit-deficient mice (−/−) or age- and sex-matched wild type mice (+/+) were injected with LPS (0.1 mg/kg, i.p.). Blood and organs were obtained either 1 h (for TNF) or 4 h (for IL-1β and IL-6) after LPS stimulation. Levels of TNF, IL-1β and IL-6 in serum or organs were measured with ELISA. Panel a: TNF levels in serum. n=10 per group. Panel b: TNF levels in liver. n=6 per group. Panel c: TNT levels in spleen. n=6 per group. Panel d: IL-1β levels in serum. n=8 per group. Panel e: IL-6 levels in serum. n=9 per group. *=P<0.05 versus wild type controls.

Macrophages are the major source of TNF produced in response to bacterial endotoxin in vivo (Bianchi et al., 1995; Kumins et al., 1996). To investigate if nicotinic acetylcholine receptor α7 subunit is essential for the cholinergic anti-inflammatory pathway in vivo, we measured TNF production in mice deficient in the α7 gene generated by genetic knockout technology (Orr-Urtreger et al., 1997). Mice lacking the α7 receptor subunit develop normally and show no gross anatomical defects (Id.; Franceschini et al., 2000). The serum TNF level in α7 subunit-deficient mice exposed to endotoxin was more than 5-fold higher than wild type control mice (wild type serum TNF=2.3±0.3 ng ml$^{-1}$ vs. α7 knockout mice serum TNF=12.2±4.7 ng ml$^{-1}$, p<0.05 (two-tailed t test) (FIG. 4a). TNF production in liver and spleen was also higher in knockout mice (FIG. 4b, c), indicating a critical function of the nicotinic acetylcholine receptor α7 subunit in the regulation of inflammatory responses in vivo. Endotoxemic α7 subunit-deficient mice also produced significantly higher levels of IL-1β (FIG. 4d) and IL-6 (FIG. 4e) as compared to wild-type mice. Macrophages derived from α7 subunit knockout mice were refractory to cholinergic agonists, and produced TNF normally in the presence of nicotine or acetylcholine (Table 1). Thus, nicotinic acetylcholine receptor α7 subunit expression in macrophages is essential for cholinergic modulation of TNF.

TABLE 1

TNF production by wild type and α7-deficient peritoneal macrophages.

| Treatment | TNF – ng ml$^{-1}$ | |
|---|---|---|
| | Wild type | α7 knockout |
| Control | 0.004 ± 0.0005 | 0.004 ± 0.0004 |
| LPS | 16.8 ± 23 | 18.1 ± 4.9 |
| LPS + nicotine (1 μM) | 5.2 ± 0.9* | 17.8 ± 0.6 |
| LPS + nicotine (10 μM) | 7.3 ± 1.0* | 17.4 ± 2.9 |
| LPS + Ach (1 μM) | 10.3 ± 1.1 | 20.4 ± 3.8 |
| LPS + Ach (10 μM) | 5.7 ± 0.9* | 21.4 ± 2.4 |

Peritoneal macrophages isolated from thioglycollate-elicited wild type mice or nicotinic acetylcholine receptor α7 subunit knockout mice were stimulated with LPS (100 ng/ml) for 4 h in culture.
Control: unstimulated macrophage cultures. Where indicated, nicotine or acetylcholine (Ach) were added 5-10 min before LPS.
TNF levels were measured by ELISA; data shown are mean ± s.e.m. n = 8 per group.
*= significantly different from LPS at $p < 0.05$ by two-tailed t test.

Figure 5:
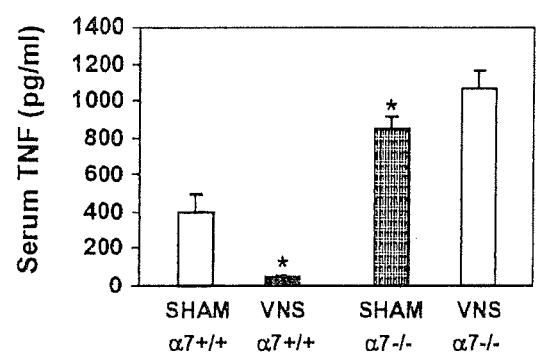
FIG. 5 is a graph showing that vagus nerve stimulation does not inhibit TNT in nicotinic acetylcholine receptor α7 subunit-deficient mice. α7 subunit-deficient mice (−/−) or age and sex matched wild-type mice (+/+) were subjected to either sham operation (SHAM) or vagus nerve stimulation (VNS, left vagus, 1 volt, 2 ins, 1 Hz); blood was collected 2 h after LPS administration. Serum TNT levels were determined by ELISA. n=10 (SHAM α7+/+). n=11 (VNS α7+/+, SHAM α7−/−, VNS α7−/−). *=P<0.05 vs SHAM α7+/+.

To determine whether nicotinic acetylcholine receptor α7 subunit is required for vagus inhibition of systemic TNF, we applied electrical stimulation (Borovikova et al., 2000) to the vagus nerves of endotoxemic wild-type or β7 subunit-deficient mice. Electrical stimulation of the vagus nerve significantly attenuated endotoxin-induced serum TNF levels in wild-type mice (FIG. 5). Vagus nerve stimulation using this protocol in nicotinic acetylcholine receptor α7 subunit deficient mice, however, failed to reduce serum TNF levels during endotoxemia (FIG. 5). Thus, a functional response to vagus nerve stimulation in vivo requires nicotinic acetylcholine receptor α7 subunits to inhibit TNF release.

These observations have several implications to understanding the regulation of inflammation and TNF release, and to the design of future therapeutics. Previous data indicate that the nicotinic acetylcholine receptor α7 subunit forms homopentameric receptors that are involved in fast chemical signaling between cells (Lindstrom, 1995; Leonard & Bertrand, 2001; Le Novere & Changeux, 1995). Neuronal nicotinic acetylcholine α7 receptors are highly permeable to calcium (Vijayaraghavan et al., 1992; Shoop et al., 2001), and we have observed that nicotine induces transient calcium influx in macrophages (data not shown). The role(s) of this increased calcium flux and the intracellular mechanisms for inhibiting TNF release require further study. Disruption of nicotinic acetylcholine receptor α7 subunit expression in vivo significantly increased endotoxin-induced TNF release and rendered ineffective the vagus nerve stimulator as a method to inhibit TNF release. This indicates that the product of the nicotinic acetylcholine receptor α7 subunit gene is essential for vagus nerve regulation of acute TNF release during the systemic inflammatory response to endotoxemia. It appears that acetylcholine release from vagus nerve endings, or perhaps other sources (e.g. lymphocytes or epithelial cells) can specifically inhibit macrophage activation. The potential exists for developing cholinergic agonists that target nicotinic acetylcholine receptor α7 subunits on peripheral immune cells for use as anti-inflammatory agents to inhibit TNF release. It may also be possible to develop vagus nerve stimulators with anti-inflammatory activity; similar devices are clinically safe, and used in the treatment of some patients with seizure disorder. TNF is a clinically validated drug target for rheumatoid arthritis and Crohn's disease, so it seems reasonable to consider a TNF inhibiting strategy that targets the nicotinic acetylcholine receptor α7 subunit.

Methods

α-Bungarotoxin Staining and Confocal Microscopy.

Isolation and culture of human macrophages was performed as described previously (Borovikova et al., 2000). Cells were differentiated for seven days in the presence of MCSF (2 ng/ml) in complete culture medium (RPMI 1640 with 10% heat-inactivated human serum). Differentiated macrophages were incubated with FITC-labeled α-bungarotoxin at 1.5 μg ml$^{-1}$ (SIGMA) in the cell culture medium at 4 C for 15 min. Where indicated, nicotine was added to a final concentration of 500 μM prior to the addition of α-bungarotoxin. Cells were washed three times with RPMI medium (GIBCO) and then fixed for 15 min at room temperature in 4% paraformaldehyde-PBS solution (pH 7.2). After fixation, cells were washed with PBS once and mounted for viewing with fluorescent confocal microscope.

RT-PCR.

Total RNA was prepared from in vitro differentiated human macrophages using TRIzol reagent. Reverse transcription and first round of PCR were performed using Titan One Tube RT-PCR Kit (Roche Molecular Biochemicals) according to the manufacturer's protocol. The second round of nested PCR was conducted using Promega 2×PCR master mix. The PCR products from nested PCR were electrophoresed on an agarose gel and recovered using the Gene Clean III Kit (Biolab) and sent for sequencing to confirm the results. The primer sets for reverse transcription and first round of PCR were: α1: sense primer 5'-CCAGACCTGAG-CAACTTCATGG-3', antisense primer 5'-AATGAGTC-GACCTGCAAACACG-3'; α: sense primer 5'-GACTGT-TCGTTTCCCAGATGG-3', antisense primer 5'-ACGAAGTTGGGAGCCGACATCA-3'; α9: sense primer 5'-CGAGATCAGTACGATGGCCTAG-3', antisense primer 5'-TCTGTGACTAATCCGCTCTTGC-3'. The primer sets for nested PCR were: α1: sense primer 5'-AT-CACCTACCACTTCGTCATGC-3', antisense primer 5'-GTATGTGGTCCATCACCATTGC-3'; α7: sense primer 5'-CCCGGCAAGAGGAGTGAAAGGT-3'; antisense primer 5'-TGCAGATGATGGTGAAGACC-3'; a sense primer 5'-AGAGCCTGTGAACACCAATGTGG-3', antisense primer 5'-ATGACTTTCGCCACCTTCTTCC-3'. For cloning of the full-length α7 cDNA, the following primers were used: 5' AGGTGCCTCTGTGGCCGCA 3' with 5' GACTACTCAG-TGGCCCTG 3'; 5' CGACACGGA-GACGTGGAG 3' with 5' GGTACGGATG-TGC-CAAGGAGT 3'; 5' CAAGGATCCGGACTCAACAT-GCGCTGCTCG3' with 5' CGGCTCGAGTCACCAGTGTGGTTACGCAAAGTC 3'.

Western Blotting and α-Bungarotoxin Pull-Down Assay.

Cells lysates were prepared by incubating PC12 or primary human macrophages with lysis buffer (150 mM NaCl, 5 mM EDTA, 50 mM Tris pH7.4, 0.02% sodium azide, 1% Triton X-100 and protease inhibitor cocktail) on ice for 90 min. Equal amounts of total protein were loaded on SDS PAGE gels for western blotting with either α7 specific antibody (Santa Cruz sc-1447) or al monoclonal antibody (Oncogene). For α-bungarotoxin pull-down assay, α-bungarotoxin (SIGMA) was conjugated to CNBr-activated Sepharose beads (Pharmacia) and then incubated with cell lysates at 4° C. overnight. The beads and bound proteins were washed four times with lysis buffer and the analyzed by western blotting with α7 specific antibodies (polyclonal: Santa Cruz H-302, monoclonal: Sigma M-220).

Antisense Oligonucleotide Experiments.

Phosphorothioate antisense oligonucleotides were synthesized and purified by Genosys. The sequences of the oligonucleotides are: ASα7: 5'-gcagcgcatgttgagtcccg-3'; ASα1: 5'-gggctccatgggctaccgga-3'; ASα10: 5'-ccccatggccctg-gcactgc-3'. These sequences cover the divergent translation initiation regions of α7, α1 and α10 genes. Delivery of the antisense oligonucleotides was carried out as in Cohen et al. (1997) at 1 μM concentration of the oligonucleotides for 24 h. For cell culture experiments, the oligonucleotide-pretreated macrophage cultures were washed with fresh medium and stimulated with 100 ng ml$^{-1}$ LPS with or without nicotine (1 μM, added 5-10 min before LPS). Four hours after LPS, the amounts of TNF released were measured by L929 assay and then verified by TNF ELISA. For α-bungarotoxin staining, pretreated cells were washed and processed for FITC-α-bungarotoxin staining as described above. Nicotine and other nicotinic acetylcholine receptor α7 subunit agonists also significantly inhibit LPS-induced TNF release in the murine macrophage-like cell line RAW264.7 (data not shown).

α7 Nicotinic Receptor Deficient Mice.

α7 nicotinic receptor-deficient mice (C57BL/6 background) and wild type littermates were purchased from The Jackson Laboratory (B6.1297-Chrna$^{7tm1Bay}$, #003232). Breedings of homozygote knockout mice or wild type mice were established to obtain progenies. Male or female mice about 8 to 12 weeks old (together with age and sex matched wild type controls) were used for endotoxin experiments. Mice were weighed individually and 0.1 mg kg$^{-1}$ LPS was given accordingly (i.p.). For TNF experiments, blood, liver and spleen were collected one hour after LPS. For IL-1β and IL-6 experiments, blood samples were collected four hours after LPS. The amounts of TNF, IL-1β and IL-6 were measured by ELISA. The genotypes of the mice were confirmed by genomic PCR strategies. Peritoneal macrophages were isolated from thioglycollate elicited (48 hours) α7 knockout and wild type male and female mice about 8 weeks old (n=8/group). Macrophages were pooled for each group and cultured overnight. Nicotine and acetylcholine were added 5-10 min before LPS (100 ng ml$^{-1}$). Pyridostigmine bromide (100 μM) was added with acetylcholine. Four hours after LPS induction, TNF levels were measured by ELISA.

Vagus Nerve Stimulation.

α7 nicotinic receptor-deficient mice (C57BL/6 background, male and female) and age and sex-matched wild type C57BL/6 mice were anaesthetized with ketamine (100 mg kg$^{-1}$, intramuscularly) and Xylazine (10 mg kg$^{-1}$, intramuscularly). Mice were either subjected to sham operation or vagus nerve stimulation (left vagus, 1 volt, 2 ms, 1 Hz) with an electrical stimulation module (STM100A, Harvard Apparatus). Stimulation was performed for 20 min (10 min before and 10 min after LPS administration). LPS was given at a lethal dose (75 mg kg$^{-1}$, intraperitoneally). Blood was collected two hours after LPS administration. TNF levels were measured by ELISA.

Statistical Analysis.

Statistical analysis was performed using two-tailed t test where indicated; $P<0.05$ is considered significant. Experiments were performed in duplicate or triplicate; for in vivo and ex vivo experiments, "n" refers to the number of animals under each condition.

Example 2

Compounds (V) and (VI) are Protective in Murine Cecal Ligation and Puncture Model of Sepsis Compounds of formulae (V) and (VI) were shown to be particularly effective in treatment of sepsis in Cecal Ligation and Puncture murine model.

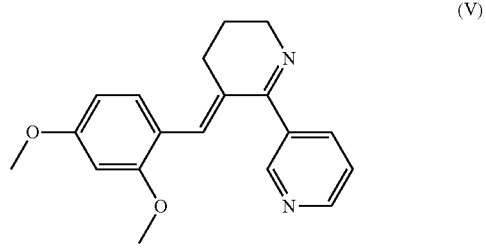

3-(2,4-dimethoxybenzylidene)anabaseine

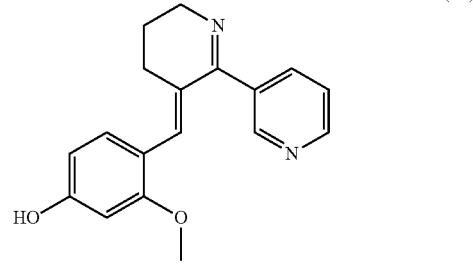

3-(4-hydroxy-2-methoxy-benzylidene)anabaseine

Cecal Ligation and Puncture (CLP) was performed as described in Fink and Heard, J. of Surg. Res. 49:186-196 (1990), Wichman et al., Crit. Care Med. 26:2078-2086 (1998) and Remick et al., Shock 4:89-95 (1995). Briefly, Balb/c mice were anesthetized with 75 mg/kg Ketamine (Fort Dodge, Fort Dodge, Iowa) and 20 mg/kg of xylazine (Bohringer Ingelheim, St. Joseph, Mo.) intramuscularly. A midline incision was performed, and the cecum was isolated. A 6-0 prolene suture ligature was placed at a level 5.0 mm from the cecal tip away from the ileocecal valve.

The ligated cecal stump was then punctured once with a 22-gauge needle, without direct extrusion of stool. The cecum was then placed back into its normal intra-abdominal position. The abdomen was then closed with a running suture of 6-0 prolene in two layers, peritoneum and fascia separately to prevent leakage of fluid. All animals were resuscitated with a normal saline solution administered sub-cutaneously at 20 ml/kg of body weight. Each mouse received a subcutaneous injection of imipenem (0.5 mg/mouse) (Primaxin, Merck & Co., Inc., West Point, Pa.) 30 minutes after the surgery. Animals were then allowed to recuperate.

Figure 6:
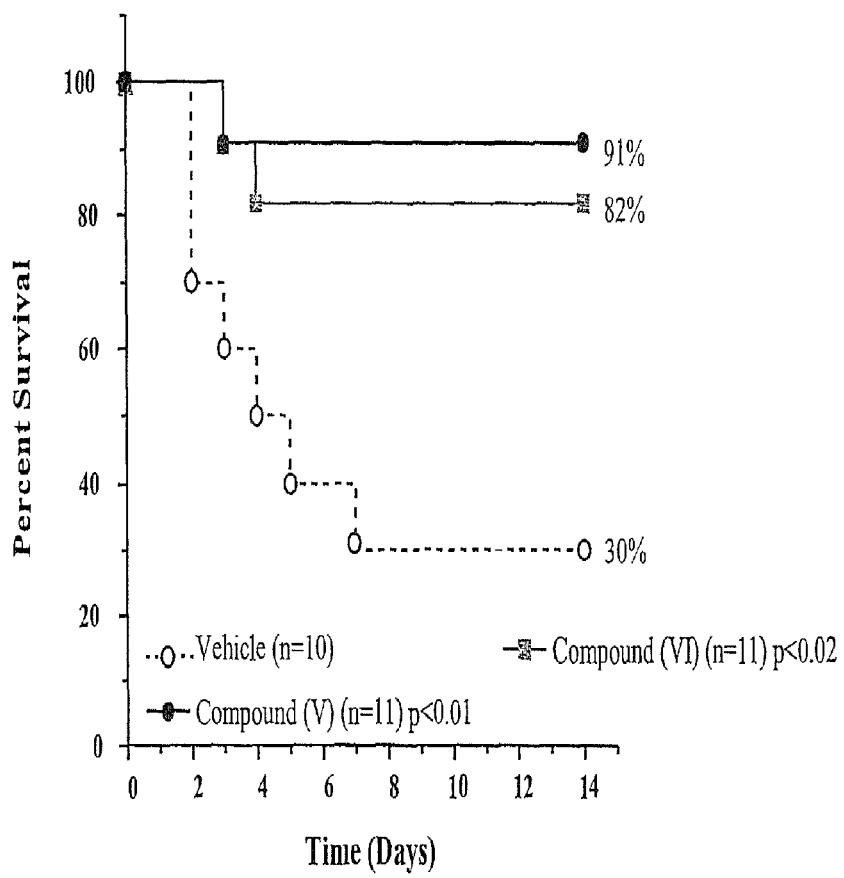
FIG. 6 is plot showing mortality (percent survival) of mice in the course of administration of either compound (V) or compound (VI) following induction of sepsis using cecal ligation and puncture model.
Figure 6:
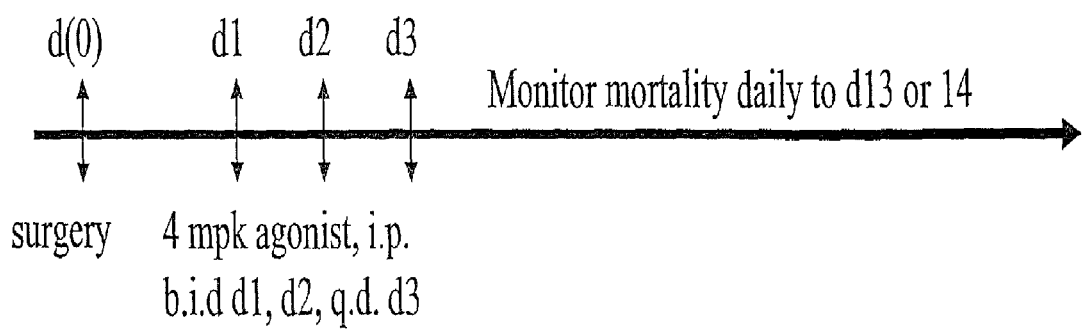

Mice were treated with either 3-2,4-dimethoxybenzylidene anabaseine (Compound (V)) at 4 mg/kg or 3-(4-hydroxy-2-methoxybenzylidene anabaseine (Compound (VI)) at 4 mg/kg or with vehicle control. The compounds and vehicle control were administered intraperitoneally (i.p.) twice a day on day 1 and day 2 (24 and 48 hours post-surgery, respectively) and were administered once on day 3. Mortality was monitored daily for fourteen days after surgery. The results are presented in FIG. 6, which shows the percentage of surviving animals following treatment with either Compound (V), Compound (VI) or vehicle control. On Day 14, 91% (p<0.01) of mice treated with Compound (V) and 82% (p<0.02) of mice treated with Compound (VI) survived whereas only 30% mice treated with the vehicle control had survived. These results demonstrate that Compounds (V) and (VI) significantly improved survival in the murine CLP model of sepsis.

Example 3

Compound (V) and Nicotine Inhibit LPS Induced TNF-α Release from Murine RAW 264.7 Macrophage-Like Cells Murine RAW 264.7 macrophage-like cells (American Type Tissue Culture Collection, Rockville, Md., USA) were grown under DMEM supplemented with 10% fetal bovine serum, penicillin and streptomycin. The cells were seeded in 24-well tissue culture plates in Opti-MEM 1 medium and used at 90% confluence. The cells were treated with either Compound (V) or nicotine (Sigma) at 0.001, 0.01, 0.1, 1, 10 or 100 uM. Five minutes after the addition of Compound (V) or nicotine, the cells were treated with LPS (500 ng/ml). Supernatants were collected after 4 hours and TNF-α was measured by ELISA (mouse ELISA kit from R&D Systems Inc., Minneapolis, Minn.).

Figure 7:
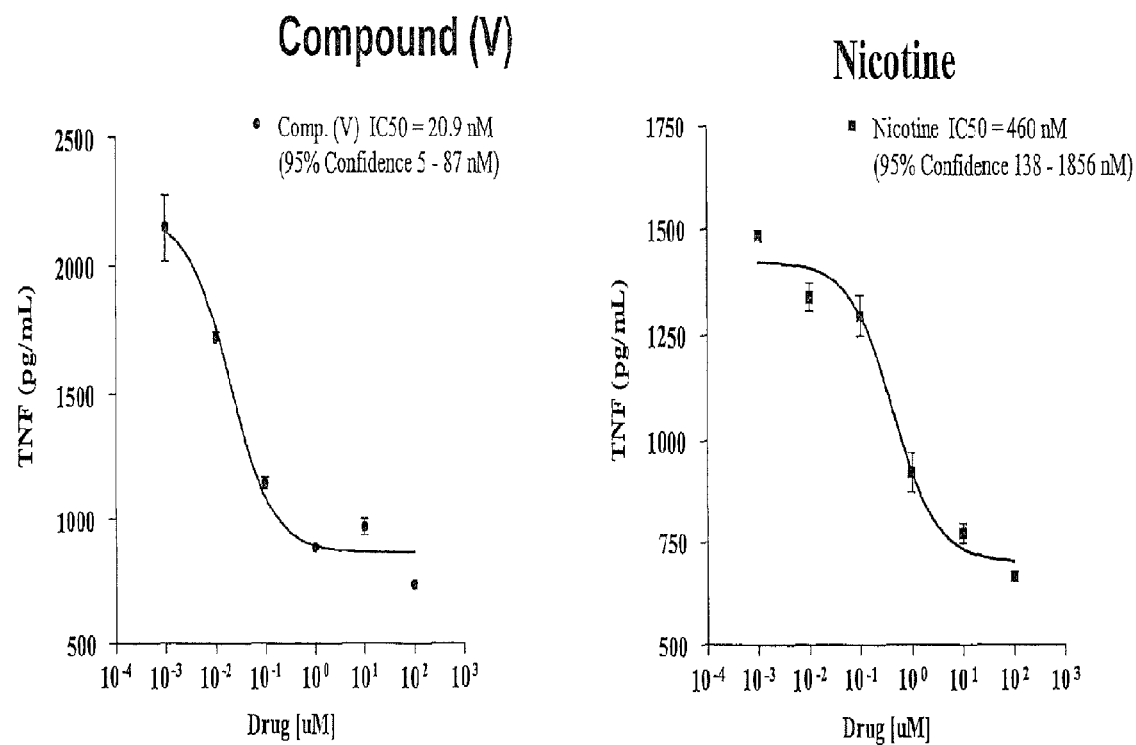
FIG. 7 is a side-by-side comparison of plots representing the measured amounts of LPS-induced release of TNF-α from murine RAW 264.7 macrophage-like cells treated with incremental concentrations of either compound (V) or nicotine as a function of concentrations of these compounds.

The results are shown in FIG. 7, which demonstrates that like nicotine, Compound (V), dose dependently inhibits TNF-α release from RAW 264.7 cells.

Example 4

Compound (VI) Inhibits LPS Induced TNF-α Release from Murine RAW 264.7 Macrophage-Like Cells Murine RAW 264.7 macrophage-like cells (American Type Tissue Culture Collection, Rockville, Md., USA) were grown under DMEM supplemented with 10% fetal bovine serum, penicillin and streptomycin. The cells were seeded in 24-well tissue culture plates in Opti-MEM 1 medium and used at 90% confluence.

In FIG. 8A, the cells were treated with Compound (VI) at 0.1, 1 and 10 uM. At 0, 1, 4 or 24 hours after preincubation with Compound (VI), the cells were treated with LPS (500 ng/ml). Supernatants were collected after 4 hours and TNF-α was measured by ELISA (mouse ELISA kit from R&D Systems Inc., Minneapolis, Minn.). The results shown in FIG. 8A are presented as percent inhibition of TNF-α. Compound (VI) dose dependently inhibits TNF-α.

FIG. 8B presents the results of the 0 hour preincubation condition of FIG. 8A and is presented as percent inhibition of TNF-α. The estimated $IC_{50}$ for Compound (VI) is 0.9 uM.

Example 5

Compound (VI) Treatment Prior to LPS Challenge Inhibits Circulating TNF in Mice

C57 B/6 mice were treated with 4 mg/kg Compound (VI) or vehicle control intraperitoneally (i.p.). Five minutes after treatment with Compound (VI) or vehicle control, the mice were injected with 100 ug LPS i.p. The mice were sacrificed 2 hours after LPS treatment and blood samples were collected for TNF-α measurement. TNF-α was measured by ELISA as described above.

Figure 9:
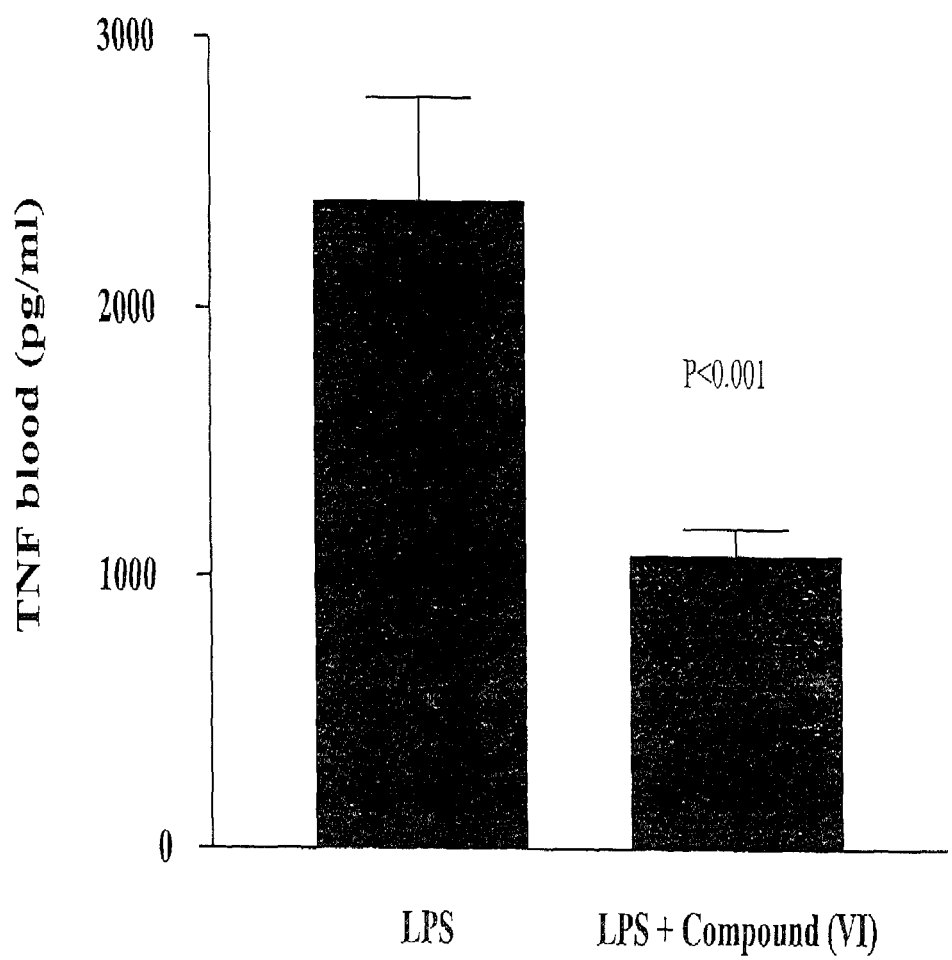
FIG. 9 is a bar plot of measured bloodstream concentration of TNF-α following administration of LPS to mice that were pre-administered compound (VI).

As shown in FIG. 9, treatment with Compound (VI) prior to LPS challenge decreased the level of circulating TNF-α by approximately 50% compared to mice treated with vehicle control.

Example 6

Compound (VI) Reduces Colon Inflammation in Murine DSS Colitis

Dextran sodium sulfate-induced (DSS) colitis was performed as described in Hove et al., Dig. Dis, Sci. 47(9): 2056-2063 (2002). C57 B/6 mice were fed 3% (w/v) DSS (mol. wt. 40 kDa; TdB Consultancy, Uppsala, Sweden) in their drinking water for seven days. 12 hours after the beginning of DSS administration, mice were injected with 4 mg/kg Compound (VI) i.p. twice a day for 7 days. Mice were sacrificed on day 7.

Figure 10:
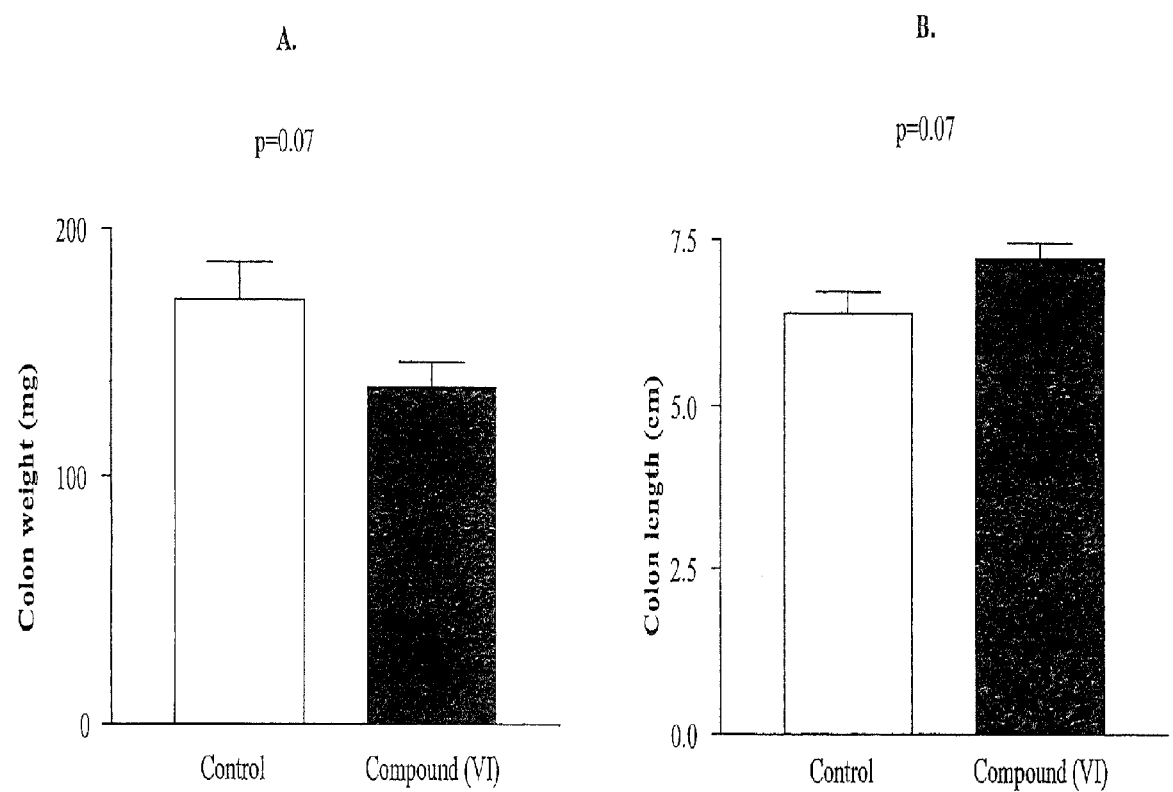
FIG. 10 is a side-by-side comparison of bar plots representing colon weight (A) and colon length (B) of mice that have been administered compound (VI) following induction of colitis by dextran sodium sulphate.

Colons were harvested after death and were removed through a midline incision. The total length of the colon was measured and the results are presented in FIG. 10(B). The shortening of the colon is indicative of a greater severity of colitis. Mice treated with Compound (VI) had a slightly greater colon length than control mice (p=0.07) indicating a lesser severity of colitis in mice treated with Compound (VI). Another indicator of disease severity, the weight of the colon was also measured. The wet weight of the colon was recorded and used as an index of inflammatory edema. The results are shown in FIG. 10 (A). Colon weight in mice treated with Compound (VI) was decreased compared to mice in the control condition. These results suggest that Compound (VI) reduces colon inflammation in murine DSS colitis.

Example 7

Compound (VII) Inhibits TNF-α Release from LPS-Stimulated Murine RAW 264.7 Macrophage-Like Cells Compound (VII) showed significant effect in inhibiting release of TNF-α.

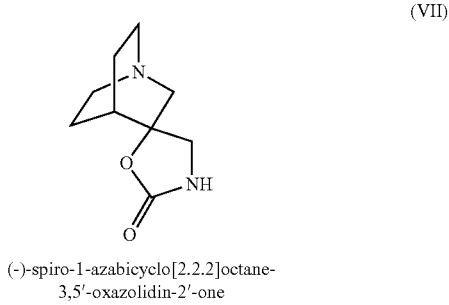

(-)-spiro-1-azabicyclo[2.2.2]octane-3,5'-oxazolidin-2'-one (VII)

Murine RAW 264.7 macrophage-like cells (American Type Tissue Culture Collection, Rockville, Md., USA) were grown as described above in Example 3. The cells were treated with (-)-spiro[1-azabicyclo[2.2.2]octane-3,5'-oxazolidin-2'-one] (Compound (VII)) at 0, 0.01, 0.1, 1, 10 and 100 uM. Five minutes after the addition of Compound (VII), the cells were treated with LPS (500 ng/ml). TNF-α was measured by ELISA as described above.

Figure 11:
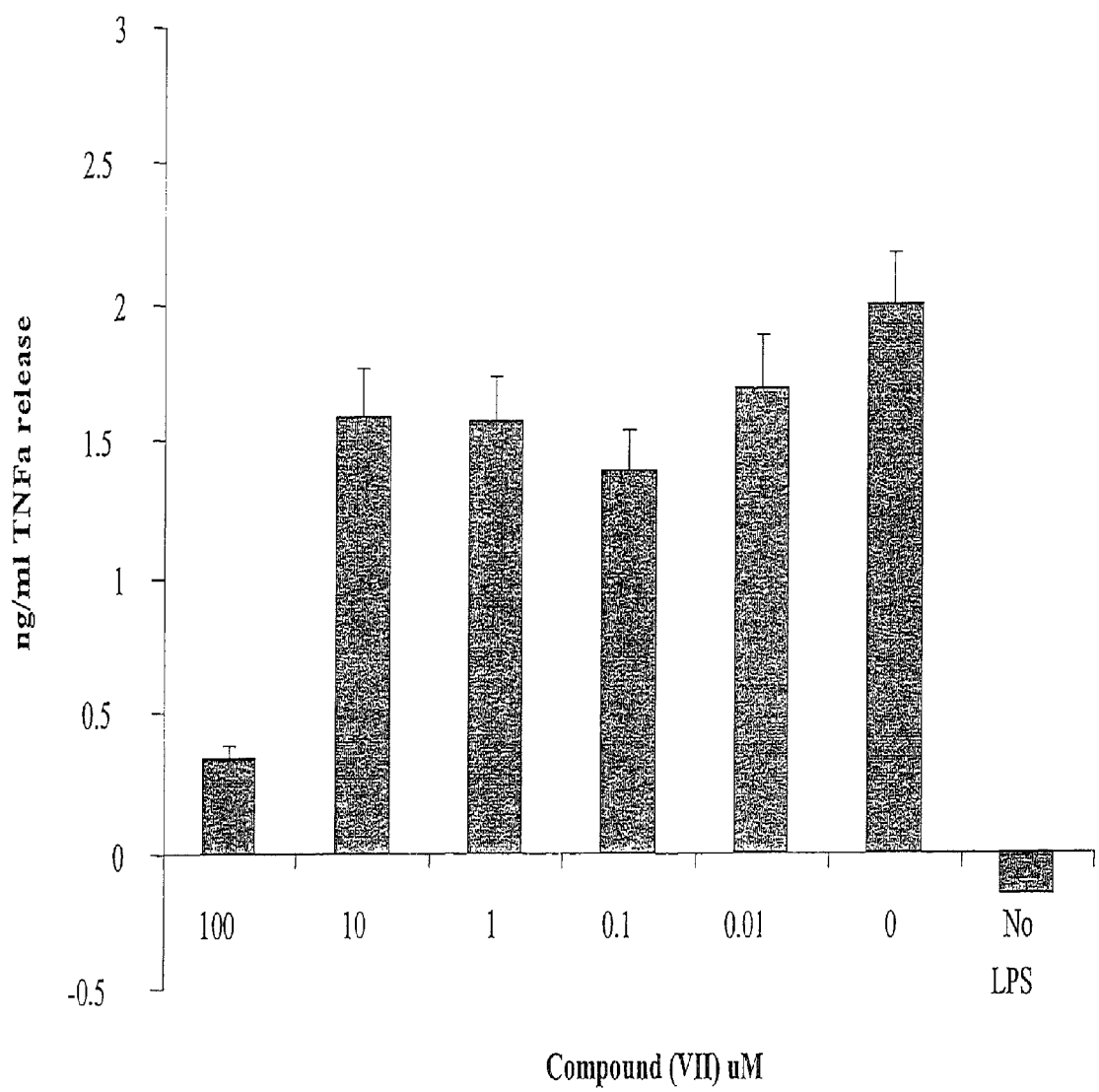
FIG. 11 is a bar plot showing the measured concentration of TNF-α released from LPS-stimulated murine RAW 264.7 macrophage-like cells following pre-incubation with incremental amounts of compound (VII).

The results are shown in FIG. 11, which demonstrate that the higher concentrations of Compound (VII) inhibit TNF-α release from RAW 264.7 cells. TNF-α release was decreased by more than four times in cells treated with 100 uM Compound (VII) compared to control cells.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating a patient suffering from a condition mediated by a proinflammatory cytokine, the method comprising administering to the patient a therapeutically effective amount of a selective α7 nicotinic receptor cholinergic agonist, wherein the condition is at least one selected from the group consisting of rheumatoid arthritis, neuritis, neuralgia, arthritis, arthralgia, fasciitis, gout, and synovitis.

2. The method of claim 1, wherein the agonist decreases the amount of the proinflammatory cytokine that is released from a macrophage in the patient.

3. The method of claim 1, wherein the cholinergic agonist is at least one selected from the group consisting of:

cocaine methiodide;

(1-aza-bicyclo[2.2.2]oct-3-yl)-carbamic acid 1-(2-fluorophenyl)-ethyl ester or a pharmaceutically acceptable salt thereof;

a compound of formula I, or a pharmaceutically acceptable salt thereof:

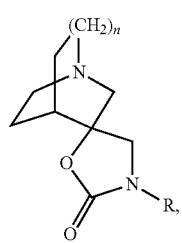

I wherein in I: R is H or CH₃, and n is 0 or 1;
a compound of formula II, or an enantiomer or pharmaceutically acceptable salt thereof:

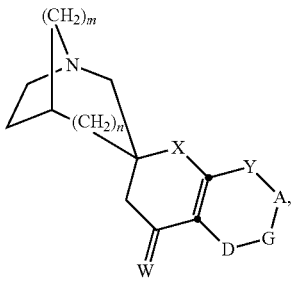

II wherein in II:
m is 1 or 2,
n is 0 or 1,
Y is CH, N or NO,
X is O or S,
W is O, H₂ or F₂,
A is N or C(R²),
G is N or C(R³),
D is N or C(R⁴),
with the proviso that no more than one of A, G and D is N but at least one of Y, A, G and D is N or NO,
$R^1$ is H or $C_1$-$C_4$ alkyl,
$R^2$, $R^3$ and $R^4$ are independently selected from the group consisting of H, halogen, $C_1$-$C_4$ alkyl, $C_2$-$C_4$ alkenyl, $C_2$-$C_4$ alkynyl, aryl, heteroaryl, OH, $OC_1$-$C_4$ alkyl, $CO_2R^1$, —CN, —NO₂, —NR⁵R⁶, —CF₃ and —OSO₂CF₃, or $R^2$ and $R^3$, $R^3$ and $R^4$, respectively, together form another six membered aromatic or heteroaromatic ring sharing A and G, or G and D, respectively, containing between zero and two nitrogen atoms, and substituted with one to two substituents independently selected from the group consisting of H, halogen, $C_1$-$C_4$ alkyl, $C_2$-$C_4$ alkenyl, $C_2$-$C_4$ alkynyl, aryl, heteroaryl, OH, $OC_1$-$C_4$ alkyl, $CO_2R^1$, —CN, —NO₂, —NR⁵R⁶, —CF₃ and —OSO₂CF₃,
$R^5$ and $R^6$ are independently selected from the group consisting of H, $C_1$-$C_4$ alkyl, C(O)R⁷, C(O)NHR⁸, C(O)OR⁹, and SO₂R¹⁰, or $R^5$ and $R^6$ together are $(CH_2)_jQ(CH_2)_k$ where Q is O, S, NR¹¹, or a bond,
j is an integer ranging from 2 to 7,
k is 0, 1 or 2,
$R^7$, $R^8$, $R^9$, $R^{10}$ and $R^{11}$ are independently selected from the group consisting of $C_1$-$C_4$ alkyl, aryl, and heteroaryl;
a compound of formula III, or a pharmaceutically acceptable salt thereof:

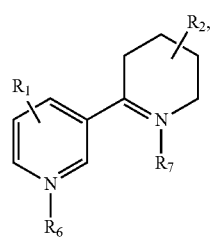

III wherein in III:
$R_1$, $R_6$ and $R_7$ are independently selected from the group consisting of H and $C_1$-$C_4$ alkyl, and $R_2$ is selected from the group consisting of:

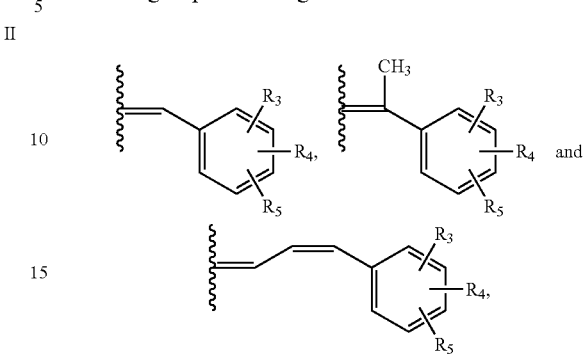

$R_3$, $R_4$ and $R_5$ are independently selected from the group consisting of H, $C_1$-$C_4$ alkyl optionally substituted with N,N-dialkylamino having 1 to 4 carbons in each of the alkyls, $C_1$-$C_6$ alkoxy optionally substituted with N,N-dialkylamino having 1 to 4 carbons in each of the alkyls, carboalkoxy having 1 to 4 carbons in the alkoxy, amino, amido having 1 to 4 carbons in the acyl, cyano, and N,N-dialkylamino having 1 to 4 carbons in each of the alkyls, halo, hydroxyl and nitro; and
a compound of formula IV, or a pharmaceutically acceptable salt thereof:

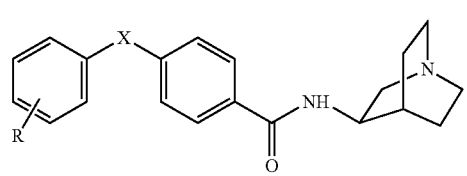

IV wherein in IV:
X is O or S, and R is selected from the group consisting of H, $OR_1$, $NHC(O)R_1$, and halogen, and
$R_1$ is $C_1$-$C_4$ alkyl.

4. The method of claim 1, wherein the cholinergic agonist is a compound of formula I, or a pharmaceutically acceptable salt thereof:

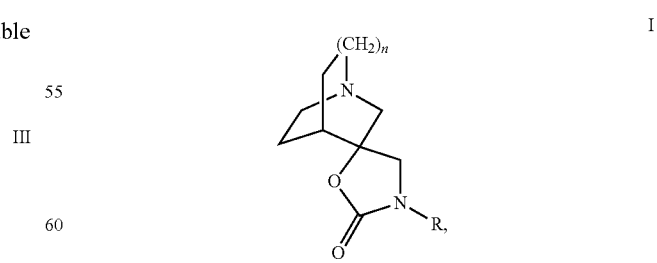

I wherein in I: R is H or CH₃, and n is 0 or 1.

5. The method of claim 4, wherein the cholinergic agonist is (−)-spiro[1-azabicyclo[2.2.2]octane-3,5'-oxazolidin-2'-one], or a pharmaceutically acceptable salt thereof:

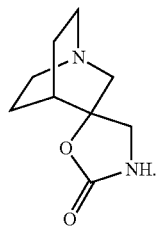

VII

6. The method of claim 1, wherein the cholinergic agonist is a compound of formula II, or an enantiomer or pharmaceutically acceptable salt thereof:

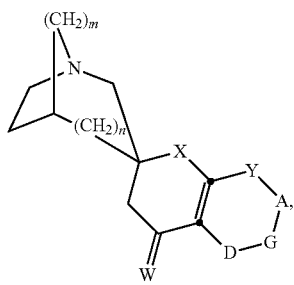

II wherein in II:
m is 1 or 2;
n is 0 or 1;
Y is CH, N or NO;
X is O or S;
W is O, $H_2$ or $F_2$;
A is N or $C(R^2)$;
G is N or $C(R^3)$;
D is N or $C(R^4)$;
with the proviso that no more than one of A, G and D is N but at least one of Y, A, G and D is N or NO;
$R^1$ is H or $C_1$-$C_4$ alkyl;
$R^2$, $R^3$ and $R^4$ are independently selected from the group consisting of H, halogen, $C_1$-$C_4$ alkyl, $C_2$-$C_4$ alkenyl, $C_2$-$C_4$ alkynyl, aryl, heteroaryl, OH, $OC_1$-$C_4$ alkyl, $CO_2R^1$, —CN, —$NO_2$, —$NR^5R^6$, —$CF_3$ and —$OSO_2CF_3$, or $R^2$ and $R^3$, $R^3$ and $R^4$, respectively, together form another six membered aromatic or heteroaromatic ring sharing A and G, or G and D, respectively, containing between zero and two nitrogen atoms, and substituted with one to two substituents independently selected from the group consisting of hydrogen, halogen, $C_1$-$C_4$ alkyl, $C_2$-$C_4$ alkenyl, $C_2$-$C_4$ alkynyl, aryl, heteroaryl, OH, $OC_1$-$C_4$ alkyl, $CO_2R^1$, —CN, —$NO_2$, —$NR^5R^6$, —$CF_3$ and —$OSO_2CF_3$;
$R^5$ and $R^6$ are independently selected from the group consisting of H, $C_1$-$C_4$ alkyl, $C(O)R^7$, $C(O)NHR^8$, $C(O)OR^9$, and $SO_2R^{10}$, or $R^5$ and $R^6$ together are $(CH_2)_jQ(CH_2)_k$ where Q is O, S, $NR^{11}$, or a bond;
j is an integer ranging from 2 to 7;
k is 0, 1 or 2;
$R^7$, $R^8$, $R^9$, $R^{10}$ and $R^{11}$ are independently selected from the group consisting of $C_1$-$C_4$ alkyl, aryl, and heteroaryl.

7. The method of claim 6, wherein the cholinergic agonist is a compound of formula II wherein m is 1; n is 0; x is oxygen; A is $C(R^2)$; G is $C(R^3)$; and D is $C(R^4)$.

8. The method of claim 6, wherein the cholinergic agonist is 5'-phenylspiro[1-azabicyclo[2.2.2]octane-3,2'-(3'H)-furo[2,3-b]pyridin] or a pharmaceutically acceptable salt thereof.

9. The method of claim 1, wherein the cholinergic agonist is a compound of formula III or a pharmaceutically acceptable salt thereof:

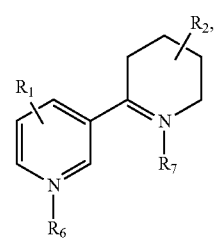

III wherein in III:
$R_1$, $R_6$ and $R_7$ are independently selected from the group consisting of H and $C_1$-$C_4$ alkyl;
$R_2$ is selected from a group of

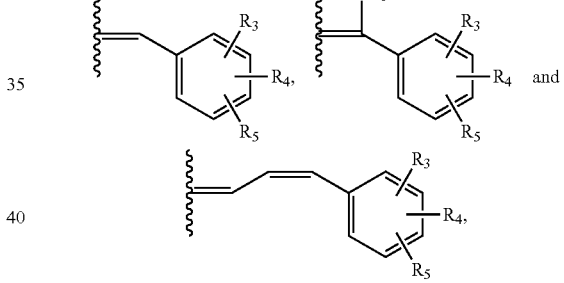

$R_3$, $R_4$ and $R_5$ are independently selected from the group consisting of H, $C_1$-$C_4$ alkyl optionally substituted with N,N-dialkylamino having 1 to 4 carbons in each of the alkyls, $C_1$-$C_6$ alkoxy optionally substituted with N,N-dialkylamino having 1 to 4 carbons in each of the alkyls, carboalkoxy having 1 to 4 carbons in the alkoxy, amino, amido having 1 to 4 carbons in the acyl, cyano, and N,N-dialkylamino having 1 to 4 carbons in each of the alkyls, halo, hydroxyl and nitro.

10. The method of claim 9, wherein the cholinergic agonist is a compound of formula III, wherein $R_2$ is attached to the 3-position of the tetrahydropyridine ring, and further wherein $R_3$, which is attached to the 4- or the 2-position of the phenyl ring, is selected from the group consisting of amino, hydroxyl, chloro, cyano, dimethylamino, methyl, methoxy, acetylamino, acetoxy, and nitro.

11. The method of claim 9, wherein the cholinergic agonist is a compound selected from the group consisting of
formula III, wherein $R_3$ is hydroxyl, and wherein $R_1$, $R_4$, and $R_5$ are H;
formula III, wherein $R_3$ is acetylamino and wherein $R_1$, $R_4$, and $R_5$ are H;

formula III, wherein R$_3$ is acetoxy and wherein R$_1$, R$_4$, and R$_5$ are H;

formula III, wherein R$_3$ is methoxy, and wherein R$_1$, R$_4$, and R$_5$ are H;

formula III, wherein R$_3$ is methoxy and wherein R$_1$ and R$_4$ are H, and further wherein R$_3$ is attached to the 2-position of the phenyl ring, and R$_5$, which is attached to the 4-position of the phenyl ring, is methoxy or hydroxy.

12. The method of claim 9, wherein the cholinergic agonist is at least one selected from the group consisting of 3-2,4-dimethoxybenzylidine anabaseine (DMXB-A), 3-(4-hydroxybenzylidene)anabaseine, 3-(4-methoxybenzylidene) anabaseine, 3-(4-aminobenzylidene)anabaseine, 3-(4-hydroxy-2-methoxybenzylidene)anabaseine, 3-(4-methoxy-2-hydroxybenzylidene)anabaseine, trans-3-cinnamylidene anabaseine, trans-3-(2-methoxy-cinnamylidene)anabaseine, trans-3-(4-methoxycinnamylidene)anabaseine, and pharmaceutically acceptable salts thereof.

13. The method of claim 12, wherein the cholinergic agonist is 3-(4-hydroxy-2-methoxybenzylidene)anabasine or a pharmaceutically acceptable salt thereof:

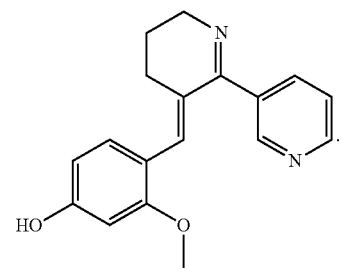

(VI)

14. The method of claim 12, wherein the cholinergic agonist is 3-(2,4-dimethoxybenzylidene)anabaseine or a pharmaceutically acceptable salt thereof:

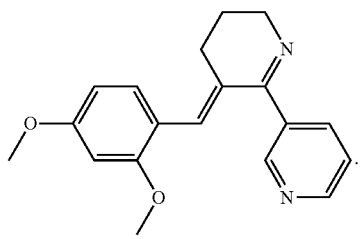

(V)

15. The method of claim 1, wherein the cholinergic agonist is a compound of formula IV or a pharmaceutically acceptable salt thereof:

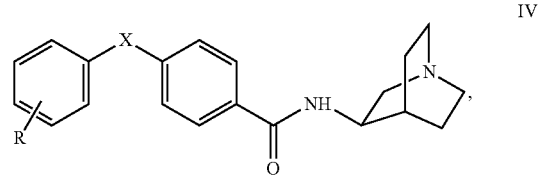

IV wherein in IV:

X is O or S; and R is selected from the group consisting of H, OR$_1$, NHC(O)R$_1$, and halogen, wherein R$_1$ is a C$_1$-C$_4$ alkyl.

16. The method of claim 15, wherein the cholinergic agonist is at least one selected from a group consisting of N-[(3R)-1-azabicyclo[2.2.2]oct-3-yl]-4-(4-hydroxyphenoxy)benzamide, N-[(3R)-1-azabicyclo[2.2.2]oct-3-yl]-4-(4-acetamidophenoxy) benzamide, N-[(3R)-1-azabicyclo[2.2.2]oct-3-yl]-4-(phenylsulfanyl)benzamide, N-[(3R)-1-azabicyclo[2.2.2]oct-3-yl]-4-(3-chlorophenylsulphonyl) benzamide, and pharmaceutically acceptable salts thereof.

17. The method of claim 15, wherein the cholinergic agonist is N-[(3R)-1-azabicyclo[2.2.2]oct-3-yl]-4-(phenylsulfanyl)benzamide or a pharmaceutically acceptable salt thereof.

18. The method of claim 1, wherein the cholinergic agonist is cocaine methiodide.

19. The method of claim 1, wherein the condition is rheumatoid arthritis.

20. The method of claim 1, wherein the condition is arthritis.

* * * * *

UNITED STATES PATENT AND TRADEMARK OFFICE
CERTIFICATE OF CORRECTION

| | |
|---|---|
| PATENT NO. | : 9,592,228 B2 |
| APPLICATION NO. | : 14/844652 |
| DATED | : March 14, 2017 |
| INVENTOR(S) | : Kevin J. Tracey and Hong Wang |

It is certified that error appears in the above-identified patent and that said Letters Patent is hereby corrected as shown below:

In the Specification

In Column 1, Lines 24-28, please replace the paragraph heading and paragraph immediately following as follows:

-- STATEMENT REGARDING FEDERALLY SPONSORED RESEARCH OR DEVELOPMENT
This invention was made with government support under grant number GM057226 awarded by the National Institutes of Health. The government has certain rights in the invention. --

Signed and Sealed this
Thirtieth Day of May, 2017

Michelle K. Lee
*Director of the United States Patent and Trademark Office*